(12) United States Patent
Bird et al.

(10) Patent No.: US 7,169,891 B2
(45) Date of Patent: Jan. 30, 2007

(54) HUMAN PELLINO POLYPEPTIDES

(75) Inventors: Timothy A Bird, Bainbridge Island, WA (US); David J Cosman, Bainbridge Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 103 days.

(21) Appl. No.: 10/258,703

(22) PCT Filed: Apr. 27, 2001

(86) PCT No.: PCT/US01/13676

§ 371 (c)(1),
(2), (4) Date: Jul. 29, 2003

(87) PCT Pub. No.: WO01/83739

PCT Pub. Date: Nov. 8, 2001

(65) Prior Publication Data

US 2004/0034199 A1    Feb. 19, 2004

Related U.S. Application Data

(60) Provisional application No. 60/200,198, filed on Apr. 28, 2000.

(51) Int. Cl.
*C07K 5/00* (2006.01)
*C12P 21/06* (2006.01)
(52) U.S. Cl. .................. 530/324; 435/69.1; 435/320.1; 435/325; 536/23.5
(58) Field of Classification Search ...................... None
See application file for complete search history.

(56) References Cited

U.S. PATENT DOCUMENTS

| 6,703,487 | B2 | 3/2004 | Bird et al. |
| 2002/0150934 | A1 | 10/2002 | Powers et al. |
| 2003/0165945 | A1 | 9/2003 | Bird et al. |
| 2004/0005615 | A1 | 1/2004 | Li et al. |

FOREIGN PATENT DOCUMENTS

| EP | 1 074 617 A2 | 2/2001 |
| WO | WO 2001/09318 A1 | 2/2001 |
| WO | WO 2001/083739 A2 | 11/2001 |
| WO | WO 2002/21138 A2 | 3/2002 |
| WO | WO 2003/059611 A2 | 8/2002 |
| WO | WO 2003/100000 A2 | 12/2003 |

OTHER PUBLICATIONS

Grosshans et al., Mech. Dev. 81: 127-138, 1999.*
Wells, 1990, Biochemistry 29:8509-8517.*
Ngo et al., The Protein Folding Problem and Tertiary Structure Prediction, pp. 491-495, 1994.*
Grosshans, J. (Reference 1), Grosshans, J. et al. (Reference 2), and Grosshans, J. and Nusslein-Volhard, C. (Reference 3), EMBL Database Accession No. AF091624, Sep. 28, 1998.
Jiang, Z. et al., "Pellino 1 is required for interleukin-1 (IL-1)-mediated signaling through its interaction with the IL-1 receptor-associated kinase 4 (IRAK4)-IRAK-tumor necrosis factor receptor-associated factor 6 (TRAF6) complex," *J. Biol. Chem.*, 278(13):10952-10956, 2003.
Kennedy, E.J. and Moynagh, P.N. (References 1 and 2), "*Homo sapiens* pellino related intracellular signalling molecule (PRISM) mRNA, complete cds", NCBI Nucleotide/GenBank Database Accession No. AF300987; Oct. 1, 2000.
Kennedy, E.J. and Moynagh, P.N., "PRISM, a novel mediator of Toll/IL-1 signalling", *FASEB J.* 15(4):A209; Mar. 7, 2001.
Li, S. et al., "IRAK-4: A novel member of the IRAK family with the properties of an IRAK-kinase," *Proc. Natl. Acad. Sci. U.S.A.*, 99(8):5567-5572, 2002.
NCBI Annotation Project, "pellino (Drosophila) homolog 2 [*Homo sapiens*]", NCBI Protein/GenBank Database Accession No. XP 007338; Feb. 10, 2001.
Ota, T. et al., "Human protein sequence SEQ ID No. 15204", GeneSeq Database Accession No. AAB94502; Jun. 26, 2001.
Resch, K. et al. (References 1 and 2), "pellino 1 [*Homo sapiens*]", NCBI Protein/GenBank Database Accession No. AF302505 1, now Accession No. AAG15393; Sep. 21, 2000.
Resch, K. et al., "Assignment of homologous genes, Peli1/PELI1 and Peli2/PELI2, for the Pelle adaptor protein Pellino to mouse chromosomes 11 and 14 and human chromosomes 2p13.3 and 14q21, respectively, by physical and radiation hybrid mapping", *Cytogenetics and Cell Genetics* 92(1-2): 172-174; 2001.
Resch, K. et al., "pellino (Drosophila) homolog 2 [*Homo sapiens*]", NCBI Protein/GenBank Database Accession No. NP 067078; Nov. 2, 2000.
Rich, T. et al. (Reference 1) and Rich, T. (Reference 2), "*Homo sapiens* mRNA for Pellino protein (ORF1)", NCBI Nucleotide/GenBank Database Accession No. AJ278859, Mar. 11, 2001.

(Continued)

*Primary Examiner*—Eileen O'Hara
*Assistant Examiner*—Gyan Chandra
(74) *Attorney, Agent, or Firm*—Patricia Anne Perkins; Suzanne Sprunger

(57) ABSTRACT

There are disclosed novel polypeptides referred to as Pellino polypeptides, as well as fragments thereof, including immunogenic peptides. DNAs encoding such polypeptides as well as methods of using such DNAs and polypeptides are also disclosed.

16 Claims, No Drawings

OTHER PUBLICATIONS

Rich, T. et al. (Reference 1) and Rich, T. (Reference 2), "Pellino [*Homo sapiens*]", NCBI Protein/GenBank Database Accession No. CAC04320; Aug. 23, 2000.

Rich, T. et al., "How low can Toll go?", *Trends in Genetics* 16(7): 292-294; Jul. 2000.

Rich, T. et al., "Pellino-related sequences from *Caenorhabditis elegans* and *Homo sapiens*", *Immunogenetics* 52: 145-149; Nov. 2000.

Rosen, C. A. et al., "Human secreted protein BLAST search protein SEQ ID No. 172", GeneSeq Database Accession No. AAB32114; Feb. 14, 2001.

Yu, K.-Y. et al., "Cutting Edge: Mouse Pellino-2 Modulates IL-1 and Lipopolysaccharide Signaling", *Journal of Immunology* 169(8): 4075-4078, Oct. 15, 2002.

* cited by examiner

SEQUENCE LISTING

<160> NUMBER OF SEQ ID NOS: 15

<210> SEQ ID NO 1
<211> LENGTH: 1257
<212> TYPE: DNA
<213> ORGANISM: Mus musculus

<400> SEQUENCE: 1

| | | | | | |
|---|---|---|---|---|---|
| atgttttctc | ctgatcaaga | aaatcatcct | tccaaagccc | cagtaaaata | tggcgaactc | 60 |
| attgtcttag | gatataatgg | atctctccca | aacggtgata | gaggaaggag | gaaaagtagg | 120 |
| tttgctttgt | ttaaaagacc | taaggcaaat | ggggtgaagc | ctagcaccgt | gcacattgca | 180 |
| tgtactcctc | aggctgccaa | ggcaataagc | aacaaggacc | agcatagcat | atcatatact | 240 |
| ttatctcgag | cccagacggt | ggtggttgaa | tatactcatg | acagcaacac | tgatatgttt | 300 |
| cagattggtc | ggtcaactga | aagtcctatt | gattttgtag | taactgacac | cgttcctgga | 360 |
| agtcagagta | attccgacac | gcagtcagta | caaagcacta | tatcaagatt | tgcctgtagg | 420 |
| atcatatgtg | agcgcagtcc | cccctttaca | gctcggattt | atgctgcagg | gtttgattca | 480 |
| tcaaaaaaca | tctttcttgg | ggagaaggct | gccaagtgga | agacatctga | tgggcagatg | 540 |
| gatggcttga | ccactaatgg | agttcttgtg | atgcatccac | gtaatgggtt | cacagaagac | 600 |
| tccaaacctg | gaatatggag | agaaatatca | gtatgtggga | atgtcttcag | tctgcgtgaa | 660 |
| accagatcag | ctcagcagag | aggaaagatg | gtggaaattg | aaaccaatca | gctacaagat | 720 |
| ggctccttaa | ttgacctttg | tggtgcaacc | ttgctgtggc | gtactgcaga | aggcctttcc | 780 |
| catactccta | ctgtgaagca | cttagaagct | ttaagacagg | agatcaatgc | agctcggccg | 840 |
| cagtgccctg | tagggttcaa | cacactagcc | ttccccagta | tgaagaggaa | ggatgttgta | 900 |
| gatgaaaagc | aaccatgggt | atatctaaac | tgcggccatg | tccatggtta | tcataactgg | 960 |
| ggaaacaaag | aagaacgtga | cggcaaagat | cgtgaatgtc | tatgtgtag | gtctgttggt | 1020 |
| ccctatgtcc | ctctgtggct | tggatgtgaa | gctggatttt | atgtggacgc | cggccctccc | 1080 |
| acccatgcct | ttagcccctg | tgggcacgtg | tgttcagaaa | agacaacggc | ttactggtcc | 1140 |
| cagatcccac | ttcctcatgg | tacgcacact | tttcatgcag | cctgcccctt | ctgtgcacat | 1200 |
| cagttggctg | gtgaacaagg | ctatatcaga | cttattttcc | aaggaccttt | agactag | 1257 |

<210> SEQ ID NO 2
<211> LENGTH: 418
<212> TYPE: PRT
<213> ORGANISM: Mus musculus

<400> SEQUENCE: 2

Met Phe Ser Pro Asp Gln Glu Asn His Pro Ser Lys Ala Pro Val Lys
1               5                   10                  15

Tyr Gly Glu Leu Ile Val Leu Gly Tyr Asn Gly Ser Leu Pro Asn Gly
                20                  25                  30

Asp Arg Gly Arg Arg Lys Ser Arg Phe Ala Leu Phe Lys Arg Pro Lys
            35                  40                  45

Ala Asn Gly Val Lys Pro Ser Thr Val His Ile Ala Cys Thr Pro Gln
        50                  55                  60

Ala Ala Lys Ala Ile Ser Asn Lys Asp Gln His Ser Ile Ser Tyr Thr
65                  70                  75                  80

Leu Ser Arg Ala Gln Thr Val Val Val Glu Tyr Thr His Asp Ser Asn
                85                  90                  95

```
Thr Asp Met Phe Gln Ile Gly Arg Ser Thr Glu Ser Pro Ile Asp Phe
            100                 105                 110

Val Val Thr Asp Thr Val Pro Gly Ser Gln Ser Asn Ser Asp Thr Gln
            115                 120                 125

Ser Val Gln Ser Thr Ile Ser Arg Phe Ala Cys Arg Ile Ile Cys Glu
            130                 135                 140

Arg Ser Pro Pro Phe Thr Ala Arg Ile Tyr Ala Ala Gly Phe Asp Ser
145                 150                 155                 160

Ser Lys Asn Ile Phe Leu Gly Glu Lys Ala Ala Lys Trp Lys Thr Ser
                165                 170                 175

Asp Gly Gln Met Asp Gly Leu Thr Thr Asn Gly Val Leu Val Met His
            180                 185                 190

Pro Arg Asn Gly Phe Thr Glu Asp Ser Lys Pro Gly Ile Trp Arg Glu
            195                 200                 205

Ile Ser Val Cys Gly Asn Val Phe Ser Leu Arg Glu Thr Arg Ser Ala
            210                 215                 220

Gln Gln Arg Gly Lys Met Val Glu Ile Glu Thr Asn Gln Leu Gln Asp
225                 230                 235                 240

Gly Ser Leu Ile Asp Leu Cys Gly Ala Thr Leu Leu Trp Arg Thr Ala
                245                 250                 255

Glu Gly Leu Ser His Thr Pro Thr Val Lys His Leu Glu Ala Leu Arg
            260                 265                 270

Gln Glu Ile Asn Ala Ala Arg Pro Gln Cys Pro Val Gly Phe Asn Thr
            275                 280                 285

Leu Ala Phe Pro Ser Met Lys Arg Lys Asp Val Val Asp Glu Lys Gln
            290                 295                 300

Pro Trp Val Tyr Leu Asn Cys Gly His Val His Gly Tyr His Asn Trp
305                 310                 315                 320

Gly Asn Lys Glu Glu Arg Asp Gly Lys Asp Arg Glu Cys Pro Met Cys
                325                 330                 335

Arg Ser Val Gly Pro Tyr Val Pro Leu Trp Leu Gly Cys Glu Ala Gly
            340                 345                 350

Phe Tyr Val Asp Ala Gly Pro Pro Thr His Ala Phe Ser Pro Cys Gly
            355                 360                 365

His Val Cys Ser Glu Lys Thr Thr Ala Tyr Trp Ser Gln Ile Pro Leu
            370                 375                 380

Pro His Gly Thr His Thr Phe His Ala Ala Cys Pro Phe Cys Ala His
385                 390                 395                 400

Gln Leu Ala Gly Glu Gln Gly Tyr Ile Arg Leu Ile Phe Gln Gly Pro
                405                 410                 415

Leu Asp

<210> SEQ ID NO 3
<211> LENGTH: 1257
<212> TYPE: DNA
<213> ORGANISM: Homo sapiens

<400> SEQUENCE: 3
atgttttctc ctgatcaaga aaatcatcca tctaaagcac cagtaaaata tggtgaactc    60
attgtcttag atataatgg atctctccca aacggtgata gaggaaggag gaaaagtagg   120
tttgctttgt ttaaaagacc taaggcaaat ggggtgaagc ccagcactgt gcatattgct   180
tgtactcctc aggctgcaaa ggcaataagc aacaaagacc agcatagcat atcatatact   240
```

```
ttatctcggg cccagactgt ggtggttgaa tatactcatg acagcaacac cgatatgttt    300
cagattggcc ggtcgactga aagccccatt gattttgtag taactgacac ggttcctgga    360
agtcaaagta attctgatac acagtcagta caaagcacta tatcaagatt tgcctgcaga    420
atcatatgtg aacggaatcc tccctttaca gcacggattt atgctgcagg gtttgactca    480
tcaaaaaaca tctttcttgg ggagaaggct gccaaatgga agacatcaga tggacagatg    540
gatggcttga ccactaatgg tgttcttgtg atgcatccac gcaatgggtt cacagaagac    600
tccaagcctg gaatatggag agaaatatcg gtgtgtggga atgtatttag cctacgtgaa    660
accagatcgg ctcagcagag aggaaaaatg gtggaaattg aaaccaatca gttacaagat    720
ggctcgttaa ttgacctctg tggtgcaaca ttgttatggc gtactgcaga aggcctttcc    780
cacactccta ccgtgaagca tttagaagct ttaagacagg aaatcaatgc agcacgacct    840
cagtgccctg tagggttcaa cacactagca tttcctagta tgaagaggaa agacgttgta    900
gatgaaaaac aaccatgggt atatctaaac tgcggccatg tacatggcta tcataactgg    960
ggaaacaaag aagaacgtga tgcaaagat cgtgaatgtc ctatgtgtag gtctgttggt   1020
ccctatgttc ctctgtggct tggatgtgaa gctggatttt atgtggacgc cggccctcca   1080
acccatgcgt ttagcccgtg tgggcatgtg tgttcagaaa agacaactgc ctattggtcc   1140
cagatcccac ttcctcatgg tactcatact tttcatgcag cctgtccctt ttgtgcacat   1200
cagttggctg gtgaacaagg ctacatcaga cttattttc aaggacctct agactaa       1257

<210> SEQ ID NO 4
<211> LENGTH: 418
<212> TYPE: PRT
<213> ORGANISM: Homo sapiens

<400> SEQUENCE: 4

Met Phe Ser Pro Asp Gln Glu Asn His Pro Ser Lys Ala Pro Val Lys
1               5                   10                  15

Tyr Gly Glu Leu Ile Val Leu Gly Tyr Asn Gly Ser Leu Pro Asn Gly
            20                  25                  30

Asp Arg Gly Arg Arg Lys Ser Arg Phe Ala Leu Phe Lys Arg Pro Lys
        35                  40                  45

Ala Asn Gly Val Lys Pro Ser Thr Val His Ile Ala Cys Thr Pro Gln
    50                  55                  60

Ala Ala Lys Ala Ile Ser Asn Lys Asp Gln His Ser Ile Ser Tyr Thr
65                  70                  75                  80

Leu Ser Arg Ala Gln Thr Val Val Glu Tyr Thr His Asp Ser Asn
            85                  90                  95

Thr Asp Met Phe Gln Ile Gly Arg Ser Thr Glu Ser Pro Ile Asp Phe
            100                 105                 110

Val Val Thr Asp Thr Val Pro Gly Ser Gln Ser Asn Ser Asp Thr Gln
        115                 120                 125

Ser Val Gln Ser Thr Ile Ser Arg Phe Ala Cys Arg Ile Ile Cys Glu
    130                 135                 140

Arg Asn Pro Pro Phe Thr Ala Arg Ile Tyr Ala Ala Gly Phe Asp Ser
145                 150                 155                 160

Ser Lys Asn Ile Phe Leu Gly Glu Lys Ala Ala Lys Trp Lys Thr Ser
                165                 170                 175

Asp Gly Gln Met Asp Gly Leu Thr Thr Asn Gly Val Leu Val Met His
            180                 185                 190

Pro Arg Asn Gly Phe Thr Glu Asp Ser Lys Pro Gly Ile Trp Arg Glu
```

```
                195                 200                 205
Ile Ser Val Cys Gly Asn Val Phe Ser Leu Arg Glu Thr Arg Ser Ala
    210                 215                 220

Gln Gln Arg Gly Lys Met Val Glu Ile Glu Thr Asn Gln Leu Gln Asp
225                 230                 235                 240

Gly Ser Leu Ile Asp Leu Cys Gly Ala Thr Leu Leu Trp Arg Thr Ala
                245                 250                 255

Glu Gly Leu Ser His Thr Pro Thr Val Lys His Leu Glu Ala Leu Arg
            260                 265                 270

Gln Glu Ile Asn Ala Ala Arg Pro Gln Cys Pro Val Gly Phe Asn Thr
        275                 280                 285

Leu Ala Phe Pro Ser Met Lys Arg Lys Asp Val Val Asp Glu Lys Gln
290                 295                 300

Pro Trp Val Tyr Leu Asn Cys Gly His Val His Gly Tyr His Asn Trp
305                 310                 315                 320

Gly Asn Lys Glu Glu Arg Asp Gly Lys Asp Arg Glu Cys Pro Met Cys
                325                 330                 335

Arg Ser Val Gly Pro Tyr Val Pro Leu Trp Leu Gly Cys Glu Ala Gly
            340                 345                 350

Phe Tyr Val Asp Ala Gly Pro Pro Thr His Ala Phe Ser Pro Cys Gly
        355                 360                 365

His Val Cys Ser Glu Lys Thr Thr Ala Tyr Trp Ser Gln Ile Pro Leu
    370                 375                 380

Pro His Gly Thr His Thr Phe His Ala Ala Cys Pro Phe Cys Ala His
385                 390                 395                 400

Gln Leu Ala Gly Glu Gln Gly Tyr Ile Arg Leu Ile Phe Gln Gly Pro
                405                 410                 415

Leu Asp

<210> SEQ ID NO 5
<211> LENGTH: 1260
<212> TYPE: DNA
<213> ORGANISM: Mus musculus

<400> SEQUENCE: 5
atgttttccc cgggccagga ggaacccagc gcccccaaca aggagccggt gaaatacggg      60
gagctggtgg tcctggggta caatggtgct ttacctaatg gtgacagggg caggaggaaa     120
agcagatttg ccctctataa gcggacctac gccagtggtg tcaaacccag cacaatccac     180
atggtctcca caccacaggc gtccaaggcc atcagctcca gaggacatca cagcatatcg     240
tacacgttgt cacggagcca gacggtagtg gtggagtaca cacacgataa agacacggac     300
atgtttcagg tgggcaggtc aacagaaagc cccattgact tcgtggtcac agacacggtt     360
tccggcggtc agaacgaaga tgcccagatc acacagagca ccatctctag gttcgcatgc     420
aggatcgtgt gtgacaggaa cgagccatat acagcacgca tattcgcggc aggattcgat     480
tcttccaaaa atatcttcct ggagagaaa gcagcaaaat ggaaaaaccc tgatggacac     540
atggatggac tcactaccaa tggtgtccta gtgatgcacc cgcaaggagg cttcaccgag     600
gaatcccagc tggagtctg gagagagatc tctgtctgtg gggatgtgta caccttgcga     660 agaccaggt cggcccagca gaggggaaag ctggtggaaa gtgagaccaa cgtcctgcaa     720
gacggctccc tcattgacct gtgtggggcc actctcctct ggagaaccgc agatggcctt     780
tttcacgctc ctactcagaa gcacatagaa gccctccggc aggagatcaa tgcagcccga     840
```

-continued

```
ccccagtgcc ccgtgggcct taacaccctg gccttcccca gcatcaaccg gaaggaagtg      900
gtggaagaga agcagccctg ggcatacctg agctgcggcc atgtgcacgg ctaccacagc      960
tggggccatc ggagcgacgc ggaagccaac gagagggagt gtcccatgtg caggactgtg     1020
ggcccctacg tccctctctg gctgggctgt gaggcaggat tttatgtcga tgcgggaccc     1080
ccaactcacg ctttcacccc ctgcgggcac gtctgttcag aaaagtctgc caagtactgg     1140
tcgcagatcc cactgcccca cggaacgcac gcgtttcatg ccgcctgtcc gttctgcgcc     1200
acgcagctgg ttggtgaaca gaactgcatc aaattgattt tccaaggtcc agtggactga     1260
```

<210> SEQ ID NO 6
<211> LENGTH: 419
<212> TYPE: PRT
<213> ORGANISM: Mus musculus

<400> SEQUENCE: 6

```
Met Phe Ser Pro Gly Gln Glu Pro Ser Ala Pro Asn Lys Glu Pro
1               5                   10                  15

Val Lys Tyr Gly Glu Leu Val Val Leu Gly Tyr Asn Gly Ala Leu Pro
            20                  25                  30

Asn Gly Asp Arg Gly Arg Arg Lys Ser Arg Phe Ala Leu Tyr Lys Arg
        35                  40                  45

Thr Tyr Ala Ser Gly Val Lys Pro Ser Thr Ile His Met Val Ser Thr
    50                  55                  60

Pro Gln Ala Ser Lys Ala Ile Ser Ser Arg Gly His His Ser Ile Ser
65                  70                  75                  80

Tyr Thr Leu Ser Arg Ser Gln Thr Val Val Glu Tyr Thr His Asp
                85                  90                  95

Lys Asp Thr Asp Met Phe Gln Val Gly Arg Ser Thr Glu Ser Pro Ile
            100                 105                 110

Asp Phe Val Val Thr Asp Thr Val Ser Gly Gly Gln Asn Glu Asp Ala
        115                 120                 125

Gln Ile Thr Gln Ser Thr Ile Ser Arg Phe Ala Cys Arg Ile Val Cys
    130                 135                 140

Asp Arg Asn Glu Pro Tyr Thr Ala Arg Ile Phe Ala Ala Gly Phe Asp
145                 150                 155                 160

Ser Ser Lys Asn Ile Phe Leu Gly Glu Lys Ala Ala Lys Trp Lys Asn
                165                 170                 175

Pro Asp Gly His Met Asp Gly Leu Thr Thr Asn Gly Val Leu Val Met
            180                 185                 190

His Pro Gln Gly Gly Phe Thr Glu Glu Ser Gln Pro Gly Val Trp Arg
        195                 200                 205

Glu Ile Ser Val Cys Gly Asp Val Tyr Thr Leu Arg Glu Thr Arg Ser
    210                 215                 220

Ala Gln Gln Arg Gly Lys Leu Val Glu Ser Glu Thr Asn Val Leu Gln
225                 230                 235                 240

Asp Gly Ser Leu Ile Asp Leu Cys Gly Ala Thr Leu Leu Trp Arg Thr
                245                 250                 255

Ala Asp Gly Leu Phe His Ala Pro Thr Gln Lys His Ile Glu Ala Leu
            260                 265                 270

Arg Gln Glu Ile Asn Ala Ala Arg Pro Gln Cys Pro Val Gly Leu Asn
        275                 280                 285

Thr Leu Ala Phe Pro Ser Ile Asn Arg Lys Glu Val Val Glu Glu Lys
    290                 295                 300
```

```
Gln Pro Trp Ala Tyr Leu Ser Cys Gly His Val Gly Tyr His Ser
305                 310                 315                 320

Trp Gly His Arg Ser Asp Ala Glu Ala Asn Glu Arg Glu Cys Pro Met
                325                 330                 335

Cys Arg Thr Val Gly Pro Tyr Val Pro Leu Trp Leu Gly Cys Glu Ala
            340                 345                 350

Gly Phe Tyr Val Asp Ala Gly Pro Thr His Ala Phe Thr Pro Cys
        355                 360                 365

Gly His Val Cys Ser Glu Lys Ser Ala Lys Tyr Trp Ser Gln Ile Pro
    370                 375                 380

Leu Pro His Gly Thr His Ala Phe His Ala Ala Cys Pro Phe Cys Ala
385                 390                 395                 400

Thr Gln Leu Val Gly Glu Gln Asn Cys Ile Lys Leu Ile Phe Gln Gly
                405                 410                 415

Pro Val Asp

<210> SEQ ID NO 7
<211> LENGTH: 1263
<212> TYPE: DNA
<213> ORGANISM: Homo sapiens

<400> SEQUENCE: 7
atgttttccc ctggccagga ggaacactgc gcccccaata aggagccagt gaaatacggg      60
gagctggtgg tgctcgggta caatggtgct ttacccaatg agatagagg acggaggaaa     120 agtagatttg ccctctacaa gcggcccaag gcaaatggtg tcaaacccag caccgtccat     180
gtgatatcca cgccccaggc atccaaggct atcagctgca aggtcaaca cagtatatcc     240 tacactttgt caaggaatca gactgtggtg gtggagtaca cacatgataa ggatacggat     300
atgtttcagg tgggcagatc aacagaaagc cctatcgact tcgttgtcac agacacgatt     360
tctggcagcc agaacacgga cgaagcccag atcacacaga gcaccatatc caggttcgcc     420
tgcaggatcg tgtgcgacag gaatgaacct tacacagcac ggatattcgc cgccggattt     480
gactcttcca aaacatatt tcttggagta aaggcagcaa agtggaaaaa ccccgacggc     540
cacatggatg ggctcactac taatggcgtc ctggtgatgc atccacgagg gggcttcacc     600
gaggagtccc agcccggggt ctggcgcgag atctctgtct gtggagatgt gtacaccttg     660
cgagaaacca ggtcggccca gcaacgagga aagctggtgg aaagtgagac caacgtcctg     720
caggacggct ccctcattga cctgtgtggg gccactctcc tctggagaac agcagatggg     780 cttttttcata ctccaactca gaagcacata gaagccctcc ggcaggagat taacgccgcc     840
cggcctcagt gtcctgtggg gctcaacacc ctggccttcc ccagcatcaa caggaaagag     900
gtggtggagg agaagcagcc ctgggcatat ctcagttgtg gccacgtgca cgggtaccac     960 aactgggggcc atcggagtga cacggaggcc aacgagaggg agtgtcccat gtgcaggact    1020
gtgggcccct atgtgcctct ctggcttggc tgtgaggcag atttatgt agacgcagga    1080 ccgccaactc atgctttcac tccctgtgga cacgtgtgct cggagaagtc tgcaaaatac    1140
tggtctcaga tcccgttgcc tcatggaact catgcatttc acgctgcttg ccctttctgt    1200
gctacacagc tggttgggga gcaaaactgc atcaaattaa ttttccaagg tccaattgac    1260
tga                                                                  1263

<210> SEQ ID NO 8
<211> LENGTH: 420
<212> TYPE: PRT
```

<213> ORGANISM: Homo sapiens

<400> SEQUENCE: 8

```
Met Phe Ser Pro Gly Gln Glu His Cys Ala Pro Asn Lys Glu Pro
 1               5                  10                  15

Val Lys Tyr Gly Glu Leu Val Val Leu Gly Tyr Asn Gly Ala Leu Pro
                20                  25                  30

Asn Gly Asp Arg Gly Arg Arg Lys Ser Arg Phe Ala Leu Tyr Lys Arg
            35                  40                  45

Pro Lys Ala Asn Gly Val Lys Pro Ser Thr Val His Val Ile Ser Thr
 50                  55                  60

Pro Gln Ala Ser Lys Ala Ile Ser Cys Lys Gly Gln His Ser Ile Ser
 65                  70                  75                  80

Tyr Thr Leu Ser Arg Asn Gln Thr Val Val Glu Tyr Thr His Asp
                85                  90                  95

Lys Asp Thr Asp Met Phe Gln Val Gly Arg Ser Thr Glu Ser Pro Ile
                100                 105                 110

Asp Phe Val Val Thr Asp Thr Ile Ser Gly Ser Gln Asn Thr Asp Glu
            115                 120                 125

Ala Gln Ile Thr Gln Ser Thr Ile Ser Arg Phe Ala Cys Arg Ile Val
    130                 135                 140

Cys Asp Arg Asn Glu Pro Tyr Thr Ala Arg Ile Phe Ala Ala Gly Phe
145                 150                 155                 160

Asp Ser Ser Lys Asn Ile Phe Leu Gly Val Lys Ala Ala Lys Trp Lys
                165                 170                 175

Asn Pro Asp Gly His Met Asp Gly Leu Thr Thr Asn Gly Val Leu Val
            180                 185                 190

Met His Pro Arg Gly Gly Phe Thr Glu Glu Ser Gln Pro Gly Val Trp
        195                 200                 205

Arg Glu Ile Ser Val Cys Gly Asp Val Tyr Thr Leu Arg Glu Thr Arg
    210                 215                 220

Ser Ala Gln Gln Arg Gly Lys Leu Val Glu Ser Glu Thr Asn Val Leu
225                 230                 235                 240

Gln Asp Gly Ser Leu Ile Asp Leu Cys Gly Ala Thr Leu Leu Trp Arg
                245                 250                 255

Thr Ala Asp Gly Leu Phe His Thr Pro Thr Gln Lys His Ile Glu Ala
            260                 265                 270

Leu Arg Gln Glu Ile Asn Ala Ala Arg Pro Gln Cys Pro Val Gly Leu
        275                 280                 285

Asn Thr Leu Ala Phe Pro Ser Ile Asn Arg Lys Glu Val Val Glu Glu
    290                 295                 300

Lys Gln Pro Trp Ala Tyr Leu Ser Cys Gly His Val His Gly Tyr His
305                 310                 315                 320

Asn Trp Gly His Arg Ser Asp Thr Glu Ala Asn Glu Arg Glu Cys Pro
                325                 330                 335

Met Cys Arg Thr Val Gly Pro Tyr Val Pro Leu Trp Leu Gly Cys Glu
            340                 345                 350

Ala Gly Phe Tyr Val Asp Ala Gly Pro Pro Thr His Ala Phe Thr Pro
        355                 360                 365

Cys Gly His Val Cys Ser Glu Lys Ser Ala Lys Tyr Trp Ser Gln Ile
    370                 375                 380

Pro Leu Pro His Gly Thr His Ala Phe His Ala Ala Cys Pro Phe Cys
385                 390                 395                 400
```

-continued

Ala Thr Gln Leu Val Gly Glu Gln Asn Cys Ile Lys Leu Ile Phe Gln
            405                 410                 415

Gly Pro Ile Asp
        420

<210> SEQ ID NO 9
<211> LENGTH: 35
<212> TYPE: DNA
<213> ORGANISM: Artificial Sequence
<220> FEATURE:
<223> OTHER INFORMATION: olignonucleotide primer

<400> SEQUENCE: 9
atattcactg aattctgatg ttttctcctg atcaa                               35

<210> SEQ ID NO 10
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 10
agtgaatatg aattcctact tatcatcgtc atctttg                             37

<210> SEQ ID NO 11
<211> LENGTH: 1338
<212> TYPE: DNA
<213> ORGANISM: Homo sapiens
<220> FEATURE:
<221> NAME/KEY: misc_feature
<222> LOCATION: (513)..(513)
<223> OTHER INFORMATION: unsure

<400> SEQUENCE: 11
atggtgctgg aaggaaaccc tgaagtgggg tccccccgaa cctcagacct ccagcaccgg      60
gggaacaagg gctcttgcgt tctctcctct cccggtgaag atgcgcagcc aggcgaggag     120
cccatcaagt atggtgaact catcgtcctg ggctacaatg ttgtctggc aagtggggac      180 aagggccgcc ggcgaagccg cctggcactg agccgccggt cgcacgccaa cggggtgaag     240
ccagacgtca tgcaccacat ctccacgccg ctcgtctcca aggcactgag taaccgtggt     300
cagcacagca tctcgtatac actgtcccgg agccactcgg tcatagtgga gtatacacat     360
gatagcgaca cagacatgtt ccagattggc cgctccacag agaacatgat tgacttcgtg     420
gtaacagaca cgtcccctgg aggagggct gccgagggcc cttctgccca gagcaccatc      480
tcccgctatg cctgccgcat cctctgtgac cgncggccac cctatactgc ccgcatctat     540
gccgctggct tcgatgcctc tagcaacatc ttccttggag agcgagcggc caaatggcgg     600
accccagatg gcctgatgga tggactgacc accaatggag tcctggtgat gcacccggca     660
ggcggcttct ccgaggactc agccccgggt gtctggcgga gatctcggt ctgtgggaat      720 gtgtacacat gcgggacag ccgctcagcc cagcagcggg gcaagctggt agaaaacgag      780
tccaacgtgc tgcaggacgg ctctctcatc gacctgtgtg ggccacact gctgtggcgc      840 acaccggcgg ggctgctgcg ggctcccaca ctgaagcaac tggaggccca gcggcaggag     900
gcaaatgcag cgcgccccca gtgccccgtg ggcctcagca ctctggcctt ccccagccca     960
gcccgtggcc gcacagcgcc cgacaaacag cagccctggg tctacgtccg ctgcgggcac    1020
gtccatggct accacggctg gggctgccgg cgggagcggg gccccagga gcgcgaatgt    1080 cctctctgcc gccttgtggg gccttatgtg cctctatggc ttggccagga ggccggcctc    1140

```
tgcctggacc ctgggccgcc tagccatgcc tttgcacctt gcggccacgt ctgctctgag    1200
aagactgccc gctactgggc ccagacacca ctgccccacg gcacccatgc tttccatgcc    1260
gcctgcccct tttgcggggc ctggcttacc ggcgagcatg gctgcgtccg cctcattttc    1320
cagggcccgc tggattag                                                 1338
```

<210> SEQ ID NO 12
<211> LENGTH: 445
<212> TYPE: PRT
<213> ORGANISM: Homo sapiens

<400> SEQUENCE: 12

```
Met Val Leu Glu Gly Asn Pro Glu Val Gly Ser Pro Arg Thr Ser Asp
1               5                   10                  15

Leu Gln His Arg Gly Asn Lys Gly Ser Cys Val Leu Ser Ser Pro Gly
            20                  25                  30

Glu Asp Ala Gln Pro Gly Glu Pro Ile Lys Tyr Gly Glu Leu Ile
        35                  40                  45

Val Leu Gly Tyr Asn Gly Cys Leu Ala Ser Gly Asp Lys Gly Arg Arg
50                  55                  60

Arg Ser Arg Leu Ala Leu Ser Arg Arg Ser His Ala Asn Gly Val Lys
65                  70                  75                  80

Pro Asp Val Met His His Ile Ser Thr Pro Leu Val Ser Lys Ala Leu
                85                  90                  95

Ser Asn Arg Gly Gln His Ser Ile Ser Tyr Thr Leu Ser Arg Ser His
            100                 105                 110

Ser Val Ile Val Glu Tyr Thr His Asp Ser Asp Thr Asp Met Phe Gln
        115                 120                 125

Ile Gly Arg Ser Thr Glu Asn Met Ile Asp Phe Val Val Thr Asp Thr
130                 135                 140

Ser Pro Gly Gly Gly Ala Glu Gly Pro Ser Ala Gln Ser Thr Ile
145                 150                 155                 160

Ser Arg Tyr Ala Cys Arg Ile Leu Cys Asp Arg Arg Pro Pro Tyr Thr
                165                 170                 175

Ala Arg Ile Tyr Ala Ala Gly Phe Asp Ala Ser Ser Asn Ile Phe Leu
            180                 185                 190

Gly Glu Arg Ala Ala Lys Trp Arg Thr Pro Asp Gly Leu Met Asp Gly
        195                 200                 205

Leu Thr Thr Asn Gly Val Leu Val Met His Pro Ala Gly Gly Phe Ser
210                 215                 220

Glu Asp Ser Ala Pro Gly Val Trp Arg Glu Ile Ser Val Cys Gly Asn
225                 230                 235                 240

Val Tyr Thr Leu Arg Asp Ser Arg Ser Ala Gln Gln Arg Gly Lys Leu
                245                 250                 255

Val Glu Asn Glu Ser Asn Val Leu Gln Asp Gly Ser Leu Ile Asp Leu
            260                 265                 270

Cys Gly Ala Thr Leu Leu Trp Arg Thr Pro Ala Gly Leu Leu Arg Ala
        275                 280                 285

Pro Thr Leu Lys Gln Leu Glu Ala Gln Arg Gln Glu Ala Asn Ala Ala
290                 295                 300

Arg Pro Gln Cys Pro Val Gly Leu Ser Thr Leu Ala Phe Pro Ser Pro
305                 310                 315                 320

Ala Arg Gly Arg Thr Ala Pro Asp Lys Gln Gln Pro Trp Val Tyr Val
                325                 330                 335
```

```
Arg Cys Gly His Val His Gly Tyr His Gly Trp Gly Cys Arg Arg Glu
            340                 345                 350

Arg Gly Pro Gln Glu Arg Glu Cys Pro Leu Cys Arg Leu Val Gly Pro
            355                 360                 365

Tyr Val Pro Leu Trp Leu Gly Gln Glu Ala Gly Leu Cys Leu Asp Pro
            370                 375                 380

Gly Pro Ser His Ala Phe Ala Pro Cys Gly His Val Cys Ser Glu
385                 390                 395                 400

Lys Thr Ala Arg Tyr Trp Ala Gln Thr Pro Leu Pro His Gly Thr His
            405                 410                 415

Ala Phe His Ala Ala Cys Pro Phe Cys Gly Ala Trp Leu Thr Gly Glu
            420                 425                 430

His Gly Cys Val Arg Leu Ile Phe Gln Gly Pro Leu Asp
            435                 440                 445

<210> SEQ ID NO 13
<211> LENGTH: 424
<212> TYPE: PRT
<213> ORGANISM: Drosophila melanogaster

<400> SEQUENCE: 13

Met Val Lys Arg Thr Asp Gly Thr Glu Ser Pro Ile Leu Ala Glu Asp
1               5                   10                  15

Gly Gly Asp Gly His Asp Lys Pro Arg Leu Arg Tyr Gly Glu Leu Val
            20                  25                  30

Ile Leu Gly Tyr Asn Gly Tyr Leu Pro Gln Gly Asp Arg Gly Arg Arg
            35                  40                  45

Arg Ser Lys Phe Val Leu His Lys Arg Thr Glu Ala Ser Gly Val Lys
    50                  55                  60

Arg Ser Lys His Tyr Ile Val Gln Ser Pro Gln Thr Ser Lys Ala Ile
65                  70                  75                  80

Leu Asp Ala Asn Gln His Ser Ile Ser Tyr Thr Leu Ser Arg Asn Gln
                85                  90                  95

Ala Val Ile Val Glu Tyr Lys Glu Asp Thr Glu Thr Asp Met Phe Gln
            100                 105                 110

Val Gly Arg Ser Ser Glu Ser Pro Ile Asp Phe Val Val Met Asp Thr
            115                 120                 125

Leu Pro Gly Asp Lys Lys Asp Ala Lys Val Met Gln Ser Thr Ile Ser
130                 135                 140

Arg Phe Ala Cys Arg Ile Leu Val Asn Arg Cys Glu Pro Ala Lys Ala
145                 150                 155                 160

Arg Ile Phe Ala Ala Gly Phe Asp Ser Ser Arg Asn Ile Phe Leu Gly
                165                 170                 175

Glu Lys Ala Thr Lys Trp Gln Asp Asn Val Glu Ile Asp Gly Leu Thr
            180                 185                 190

Thr Asn Gly Val Leu Ile Met His Pro Lys Gly Ser Phe Cys Gly Gly
            195                 200                 205

Asn Ala Lys Cys Gly Leu Trp Arg Glu Cys Ser Val Gly Gly Asp Val
    210                 215                 220

Phe Ser Leu Arg Glu Ser Arg Ser Ala Gln Gln Lys Gly Gln Pro Ile
225                 230                 235                 240

Tyr Asp Glu Cys Asn Ile Leu Gln Asp Gly Thr Leu Ile Asp Leu Cys
                245                 250                 255

Gly Ala Thr Leu Leu Trp Arg Ser Ala Glu Gly Leu Gln His Ser Pro
```

-continued

```
                260                 265                 270
Thr Lys His Asp Leu Glu Lys Leu Ile Asp Ala Ile Asn Ala Gly Arg
        275                 280                 285

Pro Gln Cys Pro Val Gly Leu Asn Thr Leu Val Ile Pro Arg Lys Val
    290                 295                 300

Asn Ile Gly Asp Gln Val Asn Gln Pro Tyr Val Tyr Leu Asn Cys Gly
305                 310                 315                 320

His Val Gln Gly His His Asp Trp Gly Gln Asp Glu Asn Thr Gly Ala
                325                 330                 335

Arg Arg Cys Pro Met Cys Leu Glu Leu Gly Pro Val Val Thr Leu Cys
            340                 345                 350

Met Gly Leu Glu Pro Ala Phe Tyr Val Asp Val Gly Ala Pro Thr Tyr
        355                 360                 365

Ala Phe Asn Pro Cys Gly His Met Ala Thr Glu Lys Thr Val Lys Tyr
    370                 375                 380

Trp Ala Asn Val Glu Ile Pro His Gly Thr Asn Gly Phe Gln Ala Val
385                 390                 395                 400

Cys Pro Phe Cys Ala Thr Pro Leu Asp Gly Ala Thr Gly Tyr Ile Lys
                405                 410                 415

Leu Ile Phe Gln Asp Asn Leu Asp
            420

<210> SEQ ID NO 14
<211> LENGTH: 455
<212> TYPE: PRT
<213> ORGANISM: Ciona intestinalis

<400> SEQUENCE: 14

Met Lys Gln Glu Gly Met Asp Val Ser Ala Ser Pro Ala Leu Ala Val
1               5                   10                  15

Ala Gly Gly Met Pro Met Asp Ile Gln Phe Glu Ala Gly Ala Ser Tyr
            20                  25                  30

His Asn Phe Ser Gln Glu Asp Ala Pro Lys Glu Asp Glu Gly Asp Ile
        35                  40                  45

Ile Tyr Gly Gln Leu Ile Val Leu Gly Thr Asn Gly Gln Leu Pro Thr
    50                  55                  60

Gly Asp Lys Gly Arg Arg Arg Ser Cys Phe Thr Leu Arg Arg Lys Arg
65                  70                  75                  80

Lys Ala Thr Gly Val Lys Pro Ser Asp Gln His Gln Val Tyr Gln Lys
                85                  90                  95

Ala Ser His Ser Glu Thr Phe Leu Ser Lys Asp His His Ser Val Ser
            100                 105                 110

Tyr Thr Leu Pro Arg Ser Val Val Val Pro Tyr Val His Asp Asp
        115                 120                 125

Asn Ser Asp Met Phe Gln Ile Gly Arg Ser Thr Glu Glu Pro Ile Asp
    130                 135                 140

Phe Val Leu Met Asp Ile Glu Ala Gly Ser Ser Ile Pro Thr Asn His
145                 150                 155                 160

Lys Pro Gln Thr Gln Pro Lys Gln Ser Thr Ile Ser Arg Phe Ala Cys
                165                 170                 175

Arg Ile Val Cys Asp Arg Glu His Pro Tyr Thr Ser Arg Ile Tyr Ala
            180                 185                 190

Ala Gly Phe Asp Thr Ser Met Asn Ile Ile Leu Gly Glu Lys Ala Pro
        195                 200                 205
```

-continued

```
Lys Trp Thr Thr Glu Gln Asn Gly Lys Lys Ile Ile Asp Gly Leu Thr
    210                 215                 220

Thr Asn Gly Val Leu Ile Met Gln Pro Lys Asn Gly Phe Ser Glu Ser
225                 230                 235                 240

Ser Thr Pro Thr Gln Trp Lys Glu Thr Ser Val Cys Gly Asn Ile Tyr
                245                 250                 255

Gln Leu Arg Glu Ser Arg Ser Ala Gln Leu Pro Gly Ile Arg Met Pro
                260                 265                 270

Glu Asp Asn Asn Val Leu Val Asn Gly Thr Leu Ile Asp Leu Cys Gly
                275                 280                 285

Ala Thr Leu Leu Trp Arg Ser Ser His Glu Arg Cys Met Pro Thr
    290                 295                 300

Pro Leu His Ile Asp Glu Leu Ile His Lys Leu Asn Leu Gly Arg Pro
305                 310                 315                 320

Gln Cys Pro Val Gly Leu Thr Thr Leu Ala Phe Pro Arg Arg Ser Lys
                325                 330                 335

Ala Thr Lys Glu Thr Glu Lys Gln Pro Trp Val Tyr Leu Gln Cys Gly
                340                 345                 350

His Val His Gly Arg Ile Glu Trp Gly Tyr Gln Gly Glu Glu Glu Arg
                355                 360                 365

Ile Cys Pro Leu Cys Arg Ser Val Gly Lys Tyr Val Pro Leu Trp Val
    370                 375                 380

Gly Gly Glu Pro Ala Phe Tyr Val Asp Ile Gly Pro Pro Ser Tyr Cys
385                 390                 395                 400

Phe Val Pro Cys Gly His Val Cys Ser Gln Lys Thr Ala Ile Tyr Trp
                405                 410                 415

Ser Gln Thr Ala Leu Pro His Gly Thr Gln Ala Tyr Ser Ala Ala Cys
                420                 425                 430

Pro Phe Cys Ala Thr Pro Leu Glu Gly Asp Leu Gly Tyr Lys Lys Leu
                435                 440                 445

Ile Phe Gln Gln Pro Leu Asp
    450                 455

<210> SEQ ID NO 15
<211> LENGTH: 458
<212> TYPE: PRT
<213> ORGANISM: Caenorhabditis elegans

<400> SEQUENCE: 15

Met Val Asp Glu Ser Glu Leu Glu Asn Gly Thr Pro Ser Pro Pro Ala
1               5                   10                  15

Tyr Ser Asn Glu Ala Ile Leu Asp Asp Ile Tyr Gly Glu Leu Ile
            20                  25                  30

Leu Leu Gly Phe Asn Gly Gln Ala Glu Asn Arg Ala Thr Ser Lys Arg
            35                  40                  45

Tyr Leu Thr Glu Lys Val Leu Arg Arg Arg Asp Ser Ala Asn Gly Ile
    50                  55                  60

Lys Lys Cys Thr Val His Asn Val Ser Thr Ser Asp Thr Lys Leu Thr
65                  70                  75                  80

Lys Asp Lys Ala Arg His Thr Val Ser Phe His Ser Asp Ser Asn Lys
                85                  90                  95
```

-continued

```
Ser Val Val Ile Glu Tyr Ala Ala Asp Pro Ser Lys Asp Met Phe Gln
            100                 105                 110

Ile Gly Arg Ala Ser Asp Asp Gln Ile Asp Phe Thr Val Ile Asp Thr
        115                 120                 125

Trp Met Phe Leu Pro Glu His Ser Asp Ala Ala Val Pro Ala Arg Pro
    130                 135                 140

Gln Ile Asp Val Leu Glu Lys Gly Asp Arg Thr Ser Thr Ile Ser Arg
145                 150                 155                 160

Phe Ala Cys Arg Ile Leu Ile Asp Arg Glu Asn Ser Asn Lys Ala Tyr
                165                 170                 175

Leu Tyr Ala Ala Gly Phe Asp Ala His Gln Asn Ile Ser Ile Asn Lys
            180                 185                 190

Lys Ser Leu Lys Trp Thr Lys Ser Asn Gly Glu Val Asp Gly Leu Thr
        195                 200                 205

Thr Asn Gly Val Leu Leu Leu His Pro Asn Lys Asp Asp Leu Leu Asp
    210                 215                 220

Asp Thr Val Asp Lys Pro Met Tyr Lys Trp Arg Glu Val Ser Ile Asn
225                 230                 235                 240

Gly Asp Val Tyr Glu Pro Arg Val Thr Arg Ser Ser Ser Ala Lys Gly
                245                 250                 255

Val Phe Val Pro Glu Trp Thr Asn Met Leu Gln Asp Gly Thr Leu Ile
            260                 265                 270

Asp Leu Cys Gly Ala Thr Ile Leu Trp Arg Thr Ala Asp Gly Leu Glu
        275                 280                 285

Arg Ser Pro Lys Met Arg Glu Leu Glu Met Ala Leu Asp Arg Leu Ser
    290                 295                 300

Ala Gly Arg Pro Gln Cys Pro Val Asn Leu Asn Thr Leu Val Ile Pro
305                 310                 315                 320

Lys Lys Arg Asn Gly Arg Gln Ile Asn Arg Arg Gln Pro Tyr Val Tyr
                325                 330                 335

Leu Gln Cys Gly His Val Gln Gly Arg His Glu Trp Gly Val Gln Glu
            340                 345                 350

Asn Ser Gly Gln Arg Ser Gly Lys Cys Pro Ile Cys Leu Val Glu Ser
        355                 360                 365

Glu Arg Ile Val Gln Leu Ser Met Gly Met Glu Pro Ser Phe His Leu
    370                 375                 380

Asp Ser Gly Val Leu Asp His Thr Phe Asn Pro Cys Gly His Met Ala
385                 390                 395                 400

Ser Lys Gln Thr Val Leu Tyr Trp Ser Arg Ile Pro Leu Pro Gln Gly
                405                 410                 415

Thr Cys Arg Tyr Asp Pro Val Cys Pro Phe Cys Tyr Gln Leu Leu Ala
            420                 425                 430

Thr Glu Arg Pro Phe Val Arg Leu Ile Phe Gln Asp Asn Cys Phe Asp
        435                 440                 445

Asp Asp Thr Ile Arg Phe Ser Asn Glu Ala
    450                 455

HUMAN PELLINO POLYPEPTIDES

This application claims the benefit under 35 U.S.C. 119(e) of U.S. provisional application Ser. No. 60/200,198, filed Apr. 28, 2000, which is incorporated by reference herein.

FIELD OF THE INVENTION

The invention is directed to molecules that are members of a polypeptide family referred to as Pellino (also called Conserved Inflammatory Signal Target (CIST)). More particularly, the present invention includes Pellino polypeptides and fragments thereof, the nucleic acids encoding such polypeptides, and fragments thereof, processes for production of recombinant forms of such polypeptides, antibodies generated against these polypeptides, transgenic and knockout cells and animals, and uses thereof.

BACKGROUND OF THE INVENTION

The Interleukin-1 (IL-1) pathway is a cellular signaling pathway is that plays a crucial role in the mammalian inflammatory response. Several different receptors and ligands are involved in this pathway, including the ligands IL-1 alpha, IL-I beta and IL-1 receptor antagonist (IL-Ira), and two IL-1 receptors referred to as IL-1 receptor Type I (IL-1RI) and IL-1 receptor Type II (IL-1RII); a soluble form of the latter also exists. Of these, it appears that IL-1RI is the signaling receptor, whereas IL-1RII does not transduce signal to a cell, but instead may be involved in regulating an IL-1-mediated response (Colotta et al., Immunol. Today 15:562; 1994). Signaling via the IL-1 pathway is complex, requiring a number of accessory molecules in addition to IL-1RI, including a receptor-associated kinase (IRAK). A serine/threonine kinase with homology to IRAK, referred to as Pelle, is found in Drosophila (for review, see Belvin and Armstrong, Annu. Rev. Cell Dev. Biol. 12:393; 1996). Another Drosophila protein, Pellino, has been reported to interact with Pelle (Grosshans et al., Mech. Dev. 81:127; 1999).

Dorsal-ventral polarization in Drosophila embryos depends upon the establishment of a gradient of nuclear localization of the Rel-like transcription factor Dorsal. The transcriptional program mediated by Dorsal results from a signaling cascade triggered by binding of an extracellular ligand Spaetzle to its receptor Toll. Intermediates of this signaling cascade include the adaptor protein Tube, the serine/threonine kinase Pelle, and Cactus, a cytosolic binding partner of Dorsal. Signals transmitted by Toll result in the degradation of Cactus, and thereby permit the nuclear importation of Dorsal. The similarity between the cytosolic domains of Toll and the mammalian interleukin-1 receptor IL1-R1 was first noted by Gay and Keith (Gay, N., and Keith, F., 1991, Nature 351: 355–356), and the number of proteins which contain the homologous regions, called the Toll/IL-1R (TIR) domain has subsequently been extended to include a larger family of receptors and intracellular signaling molecules from a variety of organisms. Those with leucine-rich repeats in their extracellular domains are broadly involved in innate immune responses and include at least ten mammalian toll-like receptors (TLRs) which initiate inflammatory responses to microbial pathogens such as peptidoglycan, bacterial lipopeptides, bacterial lipopolysaccharides, zymosan, CpG DNA, flagellin, lipoteichoic acids, and Respiratory Syncytial Virus proteins; and plant proteins such as the N resistance gene product which mediate disease resistance. Furthermore, it is now clear that an important function of Toll signaling in adult Drosophila is in controlling responses to fungal infections.

Downstream components of the Toll signaling pathway have also been evolutionarily conserved in mammalian TLR and interleukin-1 receptor signaling pathways which culminate in nuclear translocation of the transcription factor Nuclear Factor kappa B (NF-kB). Protein kinases IRAK-1 and IRAK2, close homologues of Pelle, are recruited to the activated IL-1R or TLR receptor complexes through the adaptor protein MyD88 and undergo autophosphorylation reactions. Although MyD88 is not a strict analog of Tube, both proteins contain a so-called death domain, and Tube likely serves to mediate signal transmission between Toll and Pelle, to which it binds. IRAK subsequently interacts with another adaptor molecule TRAF-6, which is homologous to the recently described D-TRAF. Signals downstream of TRAF appear to be divergent, and not all of them are fully understood, but one consequence, in mammalian cells, is the activation of the IkB kinase (IKK) complex which directly phosphorylates the inhibitory Cactus homolog IkB at two N-terminal serine residues causing its ubiquitination and degradation. Released from a cytoplasmic association with IkB, NF-kB migrates into the nucleus. Recently, a candidate for an additional intermediate in Tube-Pelle interactions was found by yeast two-hybrid screening with Pelle as a bait sequence. This protein, called Pellino, was shown to interact with catalytically-competent Pelle, but not with a mutant form of Pelle that lacked kinase activity. Although a function for Pellino was not addressed in this study, it was suggested that it could either stabilize the activated form of Pelle, or mediate an interaction with downstream Pelle substrates.

IL-1 and other pro-inflammatory cytokines have been implicated in a variety of diseases and conditions, including rheumatoid arthritis, multiple myeloma, osteoporosis, endotoxemia and sepsis, osteoarthritis, inflammatory bowel disease, and allergy. Inhibition of the signaling of IL-1 using soluble forms of IL-IRs, and the IL-1ra, have been shown to be useful in treating or ameliorating disease characterized by excess levels of IL-1 (Rosenwasser, J. Allergy Clin. Immunol. 102:344; 1998). Other parts of the IL-1 signaling pathway and other pro-inflammatory MAP kinase-activated pathways have also been the target of attempts to identify additional molecules that can be used therapeutically to intervene in conditions related to IL-1 and pro-inflammatory cytokines generally. Thus, there is a need in the art to identify novel molecules involved in the IL-1 and MAP kinase-activated pro-inflammatory signaling pathways, both as tools with which to investigate cell signaling and for use in identifying inhibitors of pro-inflammatory signaling. Of particular interest are novel polypeptides that are involved in stimulation of multiple pro-inflammatory signaling pathways, as inhibition of such polypeptides would more effectively inhibit inflammatory effects than inhibition of a pathway-specific polypeptide.

SUMMARY OF THE INVENTION

The present invention is based upon the discovery of new murine and human Pellino polypeptides, murine Pellino-1 and -2, and human Pellino-1, -2, and -3.

The invention provides an isolated polypeptide capable of stimulating MAP kinase-activated signaling pathways consisting of, consisting essentially of, or more preferably, comprising an amino acid sequence selected from the group consisting of:

(a) an amino acid sequence selected from the group consisting of SEQ ID NO:4, SEQ ID NO:8, and SEQ ID NO:12;
(b) an amino acid sequence selected from the group consisting of: amino acids x1 to x2 of SEQ ID NO:4, wherein x1 is any of amino acids 130 through 134 of SEQ ID NO:4, and x2 is any of amino acids 187 through 191 of SEQ ID NO:4; amino acids x1 to x2 of SEQ ID NO:8, wherein x1 is any of the amino acids 132 through 136 of SEQ ID NO:8, and x2 is any of amino acids 189 through 193 of SEQ ID NO:8; and amino acids x1 to x2 of SEQ ID NO:12, wherein x1 is any of the amino acids 155 through 160 of SEQ ID NO:12, and x2 is any of amino acids 212 through 217 of SEQ ID NO:12;
(c) an amino acid sequence selected from the group consisting of: amino acids x1 to x2 of SEQ ID NO:4, wherein x1 is any of amino acids 1 through 10 of SEQ ID NO:4, and x2 is any of amino acids 409 through 418 of SEQ ID NO:4; amino acids x1 to x2 of SEQ ID NO:8, wherein x1 is any of amino acids 1 through 10 of SEQ ID NO:8, and x2 is any of amino acids 410 through 419 of SEQ ID NO:8; and amino acids x1 to x2 of SEQ ID NO:12, wherein x1 is any of amino acids 1 through 10 of SEQ ID NO:12, and x2 is any of amino acids 435 through 445 of SEQ ID NO:12;
(d) an allelic variant of any of (a)–(c) above;
(e) a fragment of the amino acid sequences of any of (a)–(d) comprising at least 20 contiguous amino acids;
(f) a fragment of the amino acid sequences of any of (a)–(d), wherein a polypeptide consisting of said fragment is capable of stimulating NF-kB-dependent or p38-dependent transcription;
(g) a fragment of the amino acid sequences of any of (a)–(d) comprising RING-finger-like domain amino acid sequences;
(h) an amino acid sequence comprising at least 20 amino acids and sharing amino acid identity with the amino acid sequences of any of (a)–(g), wherein the percent amino acid identity is selected from the group consisting of: at least 75%, at least 80%, at least 85%, at least 90%, at least 95%, at least 97.5%, at least 99%, and at least 99.5%;
(i) an amino acid sequence of (h), wherein a polypeptide comprising said amino acid sequence of (h) binds to an antibody that also binds to a polypeptide comprising an amino acid sequence of any of (a)–(g); and
(j) an amino acid sequence of (h) or (i) capable of stimulating NF-kB-dependent or p38-dependent transcription.

Other aspects of the invention are isolated nucleic acids encoding polypeptides of the invention, with a preferred embodiment being an isolated nucleic acid consisting of, or more preferably, comprising a nucleotide sequence selected from the group consisting of:
(a) SEQ ID NO:3;
(b) SEQ ID NO:7;
(c) SEQ ID NO:11;
(d) an allelic variant of (a)–(c);
(e) a nucleic acid, having a length of at least 15 nucleotides, that hybridizes under conditions of moderate stringency to the nucleic acid of any of claims (a) through (d);
(f) a nucleic acid comprising a nucleotide sequence that shares nucleotide sequence identity with the nucleotide sequences of the nucleic acids of any of (a)–(e), wherein the percent nucleotide sequence identity is selected from the group consisting of: at least 70%, at least 75%, at least 80%, at least 85%, at least 90%, at least 95%, at least 97.5%, at least 99%, and at least 99.5%.

The invention provides an isolated polypeptide capable of inhibiting MAP kinase-activated signaling pathways consisting of, consisting essentially of, or more preferably, comprising an amino acid sequence selected from the group consisting of:
(a) an amino acid sequence selected from the group consisting of SEQ ID NO:4, SEQ ID NO:8, and SEQ ID NO:12, wherein amino acids 1 through x1 have been deleted from said sequence, and wherein x1 is any of amino acids 50 though 98 of said sequence;
(b) SEQ ID NO:4, wherein amino acids x1 through x2 have been deleted from said sequence, and wherein x1 is any amino acid from 99 through 178 and x2 is any amino acid from 100 through 179;
(c) SEQ ID NO:8, wherein amino acids x1 through x2 have been deleted from said sequence, and wherein x1 is any amino acid from 1 through 180 and x2 is any amino acid from 2 through 181;
(d) SEQ ID NO:12, wherein amino acids x1 through x2 have been deleted from said sequence, and wherein x1 is any amino acid from 1 through 206 and x2 is any amino acid from 2 through 207;
(e) an amino acid sequence selected from the group consisting of SEQ ID NO:4, SEQ ID NO:8, and SEQ ID NO:12, wherein one or more cysteine residues of the RING-finger-like domain have been deleted or replaced by non-cysteine residues;
(f) an allelic variant of (a)–(e);
(g) fragments of the amino acid sequences of any of (a)–(d) and (f) comprising RING-finger-like domain amino acid sequences;
(h) a fragment of the amino acid sequences of any of (a)–(g), wherein a polypeptide consisting of said fragment is capable of inhibiting NF-KB-dependent or p38-dependent transcription;
(i) amino acid sequences comprising at least 20 amino acids and sharing amino acid identity with the amino acid sequences of any of (a)–(h), wherein the percent amino acid identity is selected from the group consisting of: at least 70%, at least 75%, at least 80%, at least 85%, at least 90%, at least 95%, at least 97.5%, at least 99%, and at least 99.5%;
(j) an amino acid sequence of (i), wherein a polypeptide comprising said amino acid sequence of (i) binds to an antibody that also binds to a polypeptide comprising an amino acid sequence of any of (a)–(h); and
(k) an amino acid sequence of (i) or (j) capable of inhibiting NF-kB-dependent or p38-dependent transcription.

The invention also provides an isolated genomic nucleic acid corresponding to the nucleic acids of the invention.

Other aspects of the invention are isolated nucleic acids encoding polypeptides of the invention, allelic variants of these nucleic acids, and isolated nucleic acids, preferably having a length of at least 15 nucleotides, that hybridize under conditions of moderate stringency to the nucleic acids encoding polypeptides of the invention. In preferred embodiments of the invention, such nucleic acids encode a polypeptide having Pellino polypeptide activity or Pellino dominant-negative activity, or comprise a nucleotide sequence that shares nucleotide sequence identity with the nucleotide sequences of the nucleic acids of the invention, wherein the percent nucleotide sequence identity is selected from the group consisting of: at least 70%, at least 75%, at least 80%, at least 85%, at least 90%, at least 95%, at least 97.5%, at least 99%, and at least 99.5%.

Further provided by the invention are expression vectors and recombinant host cells comprising at least one nucleic acid of the invention, and preferred recombinant host cells wherein said nucleic acid is integrated into the host cell genome.

Also provided is a process for producing a polypeptide encoded by the nucleic acids of the invention, comprising culturing a recombinant host cell under conditions promoting expression of said polypeptide, wherein the recombinant host cell comprises at least one nucleic acid of the invention. A preferred process provided by the invention further comprises purifying said polypeptide. In another aspect of the invention, the polypeptide produced by said process is provided.

Further aspects of the invention are isolated antibodies that bind to the polypeptides of the invention, preferably monoclonal antibodies, also preferably humanized antibodies or humanized antibodies, and preferably wherein the antibody inhibits the activity of said polypeptides.

The invention additionally provides a method of designing an inhibitor of the polypeptides of the invention, the method comprising the steps of determining the three-dimensional structure of any such polypeptide, analyzing the three-dimensional structure for the likely binding sites of substrates, synthesizing a molecule that incorporates a predicted reactive site, and determining the polypeptide-inhibiting activity of the molecule.

In a further aspect of the invention, methods are provided for identifying compounds that alter Pellino polypeptide activity (or Pellino dominant-negative activity) comprising (a) mixing a test compound with a polypeptide of the invention; and (b) determining whether the test compound alters the Pellino polypeptide activity (or Pellino dominant-negative activity) of said polypeptide.

In another aspect of the invention, a method is provided identifying compounds that inhibit the binding activity of Pellino polypeptides comprising (a) mixing a test compound with a polypeptide of the invention and a binding partner of said polypeptide; and (b) determining whether the test compound inhibits the binding activity of said polypeptide.

In preferred embodiments, the binding partner is an intracellular signaling pathway molecule; more preferably, the binding partner is selected from the group consisting of TRAF2, TRAF6, IRAK, TRAF1, and TRAFs 3, 4, and 5.

The invention also provides methods for stimulating NF-kB-dependent or p38-dependent transcription, or for stimulating a cellular response to an intercellular signal molecule, comprising providing at least one compound selected from the group consisting of the polypeptides of the invention and agonists of said polypeptides; with a preferred embodiment of the method further comprising increasing said activities in a patient by administering at least one polypeptide of the invention. Preferably, the intercellular signal molecule is selected from the group consisting of interleukin-1 (IL-1), TNF-alpha, IL-18, phorbol 12-myristate 13-acetate (PMA), peptidoglycan, bacterial lipopeptides, bacterial lipopolysaccharides, zymosan, CpG DNA, flagellin, lipoteichoic acids, and Respiratory Syncytial Virus proteins. Also preferably, the cellular response is translocation of NF-kB to the cell nucleus, an increase in NF-KB-dependent transcription, or an increase in p38-dependent transcription.

Further provided by the invention is a method for inhibiting NF-kB-dependent or p38-dependent transcription, comprising providing at least one antagonist of the polypeptides of the invention; with a preferred embodiment of the method further comprising decreasing said activities in a patient by administering at least one antagonist of the polypeptides of the invention, and with a further preferred embodiment wherein the antagonist is an antibody that inhibits the activity of any of said polypeptides.

The invention additionally provides methods for preventing or treating infection by a pathogen, or for inhibiting apoptosis, comprising administering at least one compound selected from the group consisting of the polypeptides of the invention and agonists of said polypeptides; with a preferred embodiment wherein the pathogen is selected from the group consisting of prions, viruses, bacteria, fungi, algae, and protozoa.

In other aspects of the invention, methods are provided for treating cancer or an inflammatory condition comprising administering an antagonist of wild-type Pellino polypeptides of the invention; with a preferred embodiment wherein the inflammatory condition is selected from the group consisting of asthma, rheumatoid arthritis, inflammatory bowel disease, Crohn's disease, ulcerative colitis, atherosclerosis, and Alzheimer's disease.

A further embodiment of the invention provides a use for the "dominant-negative" Pellino polypeptides of the invention in the preparation of a medicament for treating an inflammatory condition; with a preferred embodiment wherein the inflammatory condition is selected from the group consisting of asthma, rheumatoid arthritis, inflammatory bowel disease, Crohn's disease, ulcerative colitis, atherosclerosis, and Alzheimer's disease.

Also comprehended within the scope of the instant invention are fusion proteins comprising any of the aforementioned polypeptides and a polypeptide selected from the group consisting of an immunoglobulin Fc domain, a FLAG peptide, a peptide comprising at least about 6 His residues, a leucine zipper, a GFP peptide, a PkA peptide, a birA peptide, and a GST peptide. Nucleic acid molecules that encode such fusion proteins are also included within the instant invention, as are recombinant expression vectors comprising any of the aforementioned DNAs, host cells transformed or transfected with such xpression vectors, and processes for preparing polypeptides, comprising culturing such host cells under conditions promoting expression, and recovering the polypeptides. The invention further provides transgenic or knockout animals generated by using the inventive DNAs. The invention further provides antibodies that specifically binds the inventive polypeptides, including monoclonal antibodies and human antibodies. Assays for identification of small molecules that regulate IL-1 signaling, utilizing an inventive peptide, are also provided.

DETAILED DESCRIPTION OF THE INVENTION

We have identified murine and human Pellino-1 and -2, and human Pellino-3, new Pellino polypeptides having structural features characteristic of the Pellino polypeptide family. By expression of one of these mammalian Pellino isoforms in COS cells, murine Pellino-1, we show that various inducers of NF-kB specifically cause Pellino- to be proteolytically processed into an insoluble form. Furthermore, we demonstrate that expression of Pellino polypeptides such as Pellino-1 and Pellino-2 strongly activates NF-kB-dependent reporter genes and augments Jun N-terminal kinase, p38 kinase, and ERK signaling mediated by IL-1, and that mutant forms of Pellino, lacking conserved motifs, suppress basal and cytokine-induced NF-kB activation, and also p38-dependent transcription. The molecules of this invention have utility as, or lead to, anti-inflammatory therapies. The discovery of the polynucleotides of the invention enables the construction of expression vectors comprising DNA that encodes polypeptides; host cells transfected or transformed with the expression vectors; development of transgenic and knockout cells and animals; isolated and purified polypeptides and fragments thereof; the use of the polynucleotides thereof as probes or primers to identify DNA encoding proteins having Pellino activity, the use of single-stranded sense or antisense oligonucleotides from the nucleic acids to inhibit expression and/or function of polynucleotide encoded by the Pellino genes; the use of such polynucleotides or polypeptides to identify small molecule inhibitors of protein association or function of Pellino; the use of such polynucleotides or polypeptides to identify other molecules involved in IL-1 signaling; the use of such polypeptides and fragments thereof to generate antibodies; and the use of such antibodies to purify the Pellino polypeptide.

The amino acid sequences of murine and human Pellino-1, murine and human Pellino-2, and human Pellino-3 polypeptide are provided in SEQ ID NOs 2, 4, 6, 8, and 12, respectively, and an alignment showing the sequence similarities between murine and human Pellino-1 and -2, human Pellino-3, and other Pellino polypeptides is presented in Table 1 in Example 1 below. The Pellino polypeptide family is remarkably well conserved, with the human family members highly similar to each other, and extremely similar to homologous Pellino family members from other species such as Mus musculus.

Typical structural elements common to members of the Pellino polypeptide family include a particularly well-conserved central domain, extending from amino acid 132 through amino acid 193 in Pellino-1 (SEQ ID NOs 2 and 4; which corresponds to amino acids 134 through 195 in SEQ ID NO:8 and amino acids 158 through 219 in SEQ ID NO:12); an absolutely conserved motif from residue 245 through residue 254 of SEQ ID NOs 2 and 4 (which corresponds to amino acids 247 through 256 in SEQ ID NO:8 and amino acids 271 through 280 in SEQ ID NO:12); and a domain ("the RING-finger-like domain"), similar to the C3HC4 RING-finger subfamily of Zinc-finger domains, from amino acid 333 through amino acid 398 of SEQ ID NOs 2 and 4 (which corresponds to amino acids 335 through 400 in SEQ ID NO:8 and amino acids 360 through 425 in SEQ ID NO:12). There are certain key cysteine residues within the RING-finger-like domain, such that substitutions of those residues are likely be associated with an altered function or lack of that function for Pellino polypeptides. The conserved cysteine residues within the Pellino polypeptides are located at positions 333, 336, 367, 371, 395, and 398 of SEQ ID NOs 2 and 4 (and at positions 335, 338, 369, 373, 397, and 400 of SEQ ID NO:8 and the corresponding positions in SEQ ID NO:6, and at positions 360, 363, 394, 398, 422, and 425 of SEQ ID NO:12). The skilled artisan will recognize that the boundaries of the regions of murine and human Pellino-1 and -2, and human Pellino-3 polypeptides described above are approximate and that the precise boundaries of such domains can also differ from member to member within the Pellino polypeptide family. However, it is clear from the above and from Table 1 that murine and human Pellino-1 and -2 and human Pellino-3 polypeptides each have an overall structure consistent with each other and with other Pellino polypeptides.

Biological activities or functions associated with murine and human Pellino-1 and -2, and human Pellino-3 polypeptides, include stimulation of MAP kinase-activated signaling pathways, such as pro-inflammatory signaling pathways, and in particular stimulation of transcription from downstream promoters such as NF-kB- and p38-dependent promoters. The ability of murine and human Pellino-1 and -2 and human Pellino-3 polypeptides to stimulate MAP kinase-activated signaling pathways is associated with many domains of the Pellino polypeptides (such as the N-terminal, central conserved domain, the RING-finger-like domain, and the C-terminal domain) or with the polypeptides in their entirety, as deletions of N- or C-terminal domains and certain modifications of key residues within murine Pellino-1 have been shown either to abolish this stimulatory activity, or to generate "dominant negative" Pellino-1 mutants which inhibit MAP kinase-activated signaling pathways. The ability of murine and human Pellino-1 and -2 and human Pellino-3 polypeptides to stimulate MAP kinase-activated signaling pathways can be determined, for example, in an assay that measures the transcription of reporter genes, such as the luciferase coding sequence or the chloramphenicol acetyltransferase (CAT) coding sequence, from downstream promoters, cush as the NF-kB-dependent IL-8 promoter or the p38-dependent CHOP promoter. Pellino polypeptides that stimulate MAP kinase-activated signaling pathways preferably have at least 10% (more preferably, at least 25%, and most preferably, at least 50%) of this stimulatory activity as compared to that of murine Pellino-1 measured in the NF-kB-dependent IL-8 promoter-luciferase reporter gene assays of Example 2.

Murine and human Pellino-1 and -2, and human Pellino-3 polypeptides, are also substrates for proteases, such as chymotrypsin-like serine proteases, and demonstrate a change in solubility in response to stimulation of cells by stimulatory molecules such as TNF-alpha and PMA. The protease-substrate activity is associated with the central domain of murine and human Pellino-1 and -2 and human Pellino-3 polypeptides, this central domain comprising residues 154 and 165 of SEQ ID NO:2 (or the corresponding residues of other Pellino polypeptides), substitutions to which have been shown to reduce the cleavage of Pellino-1. Thus, for uses requiring Pellino protease-substrate activity, preferred murine and human Pellino-1 and -2 and human Pellino-3 polypeptides include those comprising residues 154 and 165 of SEQ ID NO:2 (or the corresponding residues of other Pellino polypeptides) or having the conserved central domain, and exhibiting proteolytic cleavage in response to appropriate cell stimuli, such as treatment with TNF-alpha or PMA. Preferred murine and human Pellino-1 and -2 and human Pellino-3 polypeptides further include oligomers or fusion polypeptides comprising at least one conserved central domain of one or more murine and human Pellino-1 and -2 and human Pellino-3 polypeptides, and fragments of any of these polypeptides, exhibiting proteolytic cleavage in response to appropriate cell stimuli, such as treatment with TNF-alpha or PMA. The protease-substrate activity of murine and human Pellino-1 and -2 and human Pellino-3 polypeptides can be determined, for example, in an assay that measures the extent of Pellino polypeptide cleavage as described in Examples 3 and 4 below. Pellino polypeptides having protease-substrate activity preferably have at least 10% (more preferably, at least 25%, and most preferably, at least 50%) of the protease-substrate activity of murine Pellino-1-FLAG as measured in the assays of Examples 3 and 4.

Biological activities or functions associated with certain mutant or altered forms of murine and human Pellino-1 and -2, and human Pellino-3 polypeptides, include inhibition of MAP kinase-activated signaling pathways, such as pro-inflammatory signaling pathways, and in particular inhibition of transcription from downstream promoters such as NF-kB- and p38-dependent promoters. The ability of these mutant murine and human Pellino-1 and -2 and human Pellino-3 polypeptides to inhibit MAP kinase-activated signaling pathways is associated with alterations to certain domains of the Pellino polypeptides such as the N-terminal region, central conserved domain, and the RING-finger-like domain, as deletions of 50 or 99 N-terminal amino acids and certain modifications to the central conserved domain or the RING-finger-like domain within murine Pellino-1 have been shown to generate "dominant negative" Pellino-1 mutants which inhibit MAP kinase-activated signaling pathways (see Example 2, below). The ability of altered murine and human Pellino-1 and -2 and human Pellino-3 polypeptides to inhibit MAP kinase-activated signaling pathways can be determined, for example, in an assay that measures the transcription of reporter genes, such as the luciferase coding sequence or the chloramphenicol acetyltransferase (CAT) coding sequence, from downstream promoters, such as the NF-kB-dependent IL-8 promoter or the p38-dependent CHOP promoter. Pellino polypeptides that inhibit MAP kinase-activated signaling pathways preferably have at least 10% (more preferably, at least 25%, and most preferably, at least 50%) of this inhibitory activity as compared to that of the murine Pellino-1-FLAG "d133-156-FLAG" mutant as measured in the NF-kB-dependent IL-8 promoter-luciferase reporter gene assays of Example 2.

The term "Pellino polypeptide activity," as used herein, includes any one or more of the following: stimulation of MAP kinase-activated signaling pathways, protease-substrate activity, and host defensive activity against pathogens, as well as the ex vivo and in vivo activities of wild type Pellino polypeptides. The term "Pellino polypeptide dominant-negative activity," as used herein, includes inhibition of MAP kinase-activated signaling pathways, anti-inflammatory activity, and the ability to sequester binding partners in the insoluble cell fraction, as well as the ex vivo and in vivo activities of mutant Pellino polypeptides that demonstrate such inhibitory activities in reporter gene assays. The degree to which individual members of the Pellino polypeptide family and fragments and other derivatives of these polypeptides exhibit these activities can be determined by standard assay methods, particularly assays such as those described in Examples 2, 3, and 4 below. Exemplary assays are disclosed herein; those of skill in the art will appreciate that other, similar types of assays can be used to measure Pellino polypeptide biological activities.

Another aspect of the biological activity of Pellino polypeptides is their ability to interact with particular intracellular signaling pathway molecules such as TRAF2, TRAF6, IRAK, TRAF1, and TRAFs 3, 4, and 5, with the RING-finger-like domain of Pellino polypeptides likely involved in binding to such binding partners. The conserved central domain of Pellino polypeptides interacts with a chymotrypsin-like serine protease that cleaves Pellino polypeptides, and the N-terminal portion of Pellino polypeptides is believed to bind a factor involved in localizing Pellino peptides in, or transporting them to, the portion of the cellular environment that becomes the soluble fraction upon cell lysis. Thus, when the N-terminal portion of Pellino-1 is deleted, this Pellino polypeptide becomes constitutively localized in the insoluble fraction, but is still be able to inhibit MAP kinase-activated signaling pathways, likely by binding signaling pathway polypeptides via its RING-finger-like domain. The term "binding partner," as used herein, includes ligands, receptors, substrates, antibodies, other Pellino polypeptides, the same Pellino polypeptide (in the case of homotypic interactions), and any other molecule that interacts with a Pellino polypeptide through contact or proximity between particular portions of the binding partner and the Pellino polypeptide. Because the RING-finger-like domain of Pellino polypeptides is believed to bind to a signaling pathway binding partner, the RING-finger-like domain when expressed as a separate fragment from the rest of a Pellino polypeptide, but with enough of the N-terminal domain to allow the Pellino polypeptide to localize to the insoluble fraction, is expected to disrupt the binding of wild-type Pellino polypeptides to their binding partners. Particularly suitable assays to detect or measure the binding between Pellino polypeptides and their binding partners include the bioluminescence resonance energy transfer (BRET), which uses a bioluminescent luciferase that is genetically fused to one candidate protein, such as a Pellino polypeptide, and a green fluorescent protein mutant fused to another protein of interest, such as TRAF2, IRAK, TRAF6, or other potential binding partners. Interactions between the two fusion proteins can bring the luciferase and green fluorescent protein close enough for resonance energy transfer to occur, thus changing the color of the bioluminescent emission. Most preferably, the partner-binding activities of Pellino polypeptides can be determined using protein-fragment complementation assays, as described in Remy and Michnick, 1999, *Proc Natl Acad Sci USA* 96: 5394–5399 and in WO 01/00866.

Pellino polypeptides such as murine and human Pellino-1 and -2 and human Pellino-3 polypeptides with the ability to stimulate MAP kinase-activated pathways are believed to play a role in protection of the host against viral, bacterial, fungal, and other types of pathogens (innate immune responses). In addition, Pellino polypeptides are involved in immune and/or inflammatory diseases or conditions, that share as a common feature stimulation of MAP kinase-activated pathways and NF-kB- and/or p38-dependent transcription in their etiology. The therapeutic effect of stimulation of MAP kinase-activated pathways, for example by administration of a Pellino polypeptide with wild-type activity, or fragments or fusion polypeptides with wild-type activity, or agonists thereof, is shown by the following examples of conditions in which the stimulation of NF-kB-dependent transcription is beneficial (Yamamoto and Gaynor, 2001, *J Clin Invest* 107: 135–142). The NF-kB pathway modulates B-lymphocyte survival, mitogen-dependent cell proliferation, and isotype switching, which lead to the differentiation of B lymphocytes into plasma cells. In addition, NF-kB regulates IL-2 production, which increases the proliferation and differentiation of T lymphocytes, and increases the development of Th1-type helper T cells, promoting cell-mediated immunity. Thus, activation of NF-kB leads to the induction of multiple genes that regulate the immune response. The NF-kB pathway is also a key mediator of genes involved in the control of the cellular proliferation and apoptosis. Antiapoptotic genes that are directly activated by NF-kB include the cellular inhibitors of apoptosis (c-IAP1, c-IAP2, and IXAP), the TNF receptor-associated factors (TRAF1 and TRAF2), the Bcl-2 homologue A1/Bfl-1, and IEX-IL. These antiapoptotic proteins block the activation of caspase-8, an initiator protease, involved at an early step in stimulating the apoptotic pathway, and induction of A1/Bfl-1 expression by NF-kB prevents cytochrome c release from mitochondria and activation of caspase-3. By increasing the expression of antiapoptotic cellular proteins, NF-kB activation can thus reduce apoptosis in response to treatment with different chemotherapeutic agents. In addition, NF-kB is involved in protecting cells from undergoing apoptosis in response to DNA damage or cytokine treatment.

The therapeutic effect of inhibition of MAP kinase-activated pathways, for example by administration of a Pellino polypeptide with "dominant-negative" inhibitory activity, or fragments or fusion polypeptides thereof having "dominant-negative" inhibitory activity, or other antagonists of Pellino polypeptides having wild-type activity, is shown by the following examples of conditions in which the inhibition of NF-kB-dependent transcription is beneficial (Yamamoto and Gaynor, 2001, *J Clin Invest* 107: 135–142). NF-kB regulates host inflammatory responses by increasing the expression of specific cellular genes, including genes encoding at least 27 different cytokines and chemokines. Cytokines that are stimulated by NF-kB, such as IL-1beta and TNF-alpha, can also directly activate the NF-kB pathway, thus establishing a positive autoregulatory loop that can amplify the inflammatory response and increase the duration of chronic inflammation. NF-kB also stimulates the expression of enzymes whose products contribute to the pathogenesis of the inflammatory process, including the inducible form of nitric oxide synthase (iNOS), which generates nitric oxide (NO), and the inducible cyclooxygenase (COX-2), which generates prostanoids. Activation of the NF-kB pathway is involved in the pathogenesis of chronic inflammatory diseases, such as asthma, rheumatoid arthritis, and inflammatory bowel disease, and other diseases in which inflammation plays a role, such as atherosclerosis and Alzheimer's disease. Several lines of evidence suggest that NF-kB activation of cytokine genes is an important contributor to the pathogenesis of asthma, which is characterized by the infiltration of inflammatory cells and the dysregulation of many cytokines and chemokines in the lung. Cytokines, such as TNF-alpha, that activate NF-kB are elevated in the synovial fluid of patients with rheumatoid arthritis and contribute to the chronic inflammatory changes and synovial hyperplasia seen in the joints of these patients. Increases in the production of proinflammatory cytokines by both lymphocytes and macrophages has also been implicated in the pathogenesis of inflammatory bowel diseases, including Crohn's disease and ulcerative colitis. NF-kB activation is seen in mucosal biopsy specimens from patients with active Crohn's disease and ulcerative colitis. Treatment of patients with inflammatory bowel diseases with steroids decreases NF-kB activity in biopsy specimens and reduces clinical symptoms. These results suggest that stimulation of the NF-kB pathway may be involved in the enhanced inflammatory response associated with these diseases. Atherosclerosis is triggered by numerous insults to the endothelium and smooth muscle of the damaged vessel wall. A large number of growth factors, cytokines, and chemokines released from endothelial cells, smooth muscle, macrophages, and lymphocytes are involved in this chronic inflammatory and fibroproliferative process. Regulation of genes involved in the inflammatory response and in the control of cellular proliferation by NF-kB likely plays an important role in the initiation and progression of atherosclerosis. Abnormalities in the regulation of the NF-kB pathway may be involved in the pathogenesis of Alzheimer's disease. For example, NF-kB immunoreactivity is found predominantly in and around early neuritic plaque types in Alzheimer's disease, whereas mature plaque types show vastly reduced NF-kB activity. Thus, NF-kB activation may be involved in the initiation of neuritic plaques and neuronal apoptosis during the early phases of Alzheimer's disease. Other conditions in which inflammation plays a role and which are expected to be ameliorated by decreases in MAP kinase-activated proinflammatory signaling pathways include osteoporosis, stroke, multiple sclerosis, and multiple myeloma. Additional examples of diseases involving inflammation and/or inflammatory cellular responses are described U.S. Pat. No. 6,204,261 at column 206, line 25, through column 207, line 44; this material from U.S. Pat. No. 6,204,261 is incorporated by reference herein. In addition to a role in the pathogenesis of diseases characterized by increases in the host inflammatory response, constitutive activation of the NF-kB pathway has also been implicated in the pathogenesis of some human cancers. Abnormalities in the regulation of the NF-kB pathway are frequently seen in a variety of human malignancies including leukemias, lymphomas, and solid tumors. These abnormalities result in constitutively high levels of NF-kB in the nucleus of a variety of tumors including breast, ovarian, prostate, and colon cancers. The majority of these changes are likely due to alterations in regulatory proteins that activate signaling pathways that lead to activation of the NF-kB pathway. Preventing, blocking, and/or inhibiting the interactions between Pellino polypeptides and their binding partners is an aspect of the invention and provides methods for treating or ameliorating these diseases and conditions through the use of inhibitors of wild-type Pellino activities such as stimulation of NF-kB-dependent transcription.

Polynucleotide Molecules

In a particular embodiment, the invention relates to certain isolated polynucleotide molecules that are free from contaminating endogenous material. "Polynucleotide molecule" refers to polynucleotide molecules in the form of separate fragments or as a component of larger polynucleotide constructs. The polynucleotide molecules have preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Polynucleotide molecules of the invention include DNA in both single-stranded and double-stranded form, as well as the corresponding complementary sequences. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NOs:1, 3, 5, or 7, or a suitable fragment thereof, as a probe. The DNA molecules of the invention include DNAs encoding full length Pellino polypeptides as well as polynucleotides and fragments thereof. The polynucleotides of the invention are preferentially derived from human sources, but the invention includes those derived from non-human species, as well.

The present invention encompasses murine Pellino-1 DNA having the polynucleotide sequence of SEQ ID NO:1 and the polypeptide encoded by the DNA of SEQ ID NO:1 having the amino acid sequence of SEQ ID NO:2. The polypeptide having amino acids 132 through 189 of SEQ ID NO:2 is a target site for protease action for a member of the chymotrypsin family of proteases. The present invention further encompasses human Pellino-1 DNA having the polynucleotide sequence of SEQ ID NO:3 and the polypeptide encoded by the DNA of SEQ ID NO:3 having the amino acid sequence of SEQ ID NO:4. A specific protease target site is also found in this polypeptide, corresponding to amino acids 132 through 189 of SEQ ID NO:4. Further encompassed by the present invention is the DNA of murine Pellino-2 and having the polynucleotide sequence of SEQ ID NO:5, and polypeptide encoded by SEQ ID NO:5 shown in SEQ ID NO:6. The protease target site is located between amino acids 133 and 190 of murine Pellino-2. Similarly, the protease target site of human Pellino-2 is likely to be between amino acids 134 and 191 of SEQ ID NO:8. The above described protease target sequences of SEQ ID NO:2, SEQ ID NO:4, and SEQ ID NO:6 may vary by one or more amino acids. Thus, the amino terminus of the protease target region for SEQ ID NO:2 and SEQ ID NO:4 may occur from amino acid 130 through 134 and the carboxy terminus of the target region from amino acid 187 through 191. Similarly, for SEQ ID NO:6, the amino terminus of the protease target region occurs from amino acid 131 through amino acid 135 (amino acids 132 through 136 of SEQ ID NO:8) and the carboxy terminus from amino acid 188 through 192 (amino acids 189 through 193 of SEQ ID NO:8).

Due to the known degeneracy of the genetic code, wherein more than one codon can encode the same amino acid, a DNA can vary from that shown in SEQ ID NO:1, and still encode a polypeptide having the amino acid sequence of SEQ ID NO:2. Such variant DNAs can result from silent mutations that occur naturally, or during PCR amplification, or they can be the product of deliberate mutagenesis of a native sequence. The same is true for the DNAs depicted in SEQ ID NOs: 3, 5 and 7.

The invention thus provides isolated DNAs encoding polypeptides of the invention, selected from: (a) a DNA comprising the nucleotide sequence of SEQ ID NO:1; (b) a DNA comprising the nucleotide sequence of SEQ ID NO:3; (c) a DNA comprising the nucleotide sequence of SEQ ID NO:5; (d) a DNA encoding the polypeptides encoded by the DNA of (a), (b) or (c); (e) a DNA capable of hybridization to the DNA of (a), (b) or (c) under conditions of moderate stringency and which encodes a polypeptide of the invention; (f) a DNA capable of hybridization to the DNA of (a), (b) , or (c) under conditions of high stringency and which encodes a polypeptide of the invention, and (g) a DNA which is degenerate as a result of the genetic code to a DNA defined in (a), (b), (c), (d), (e), or (f) and which encodes a polypeptide of the invention.

The basic parameters affecting the choice of hybridization conditions and guidance for devising suitable conditions are set forth by Sambrook et al., 1989. As used herein, conditions of moderate stringency can be readily d termined by those having ordinary skill in the art based on, for example, the length and/or base composition of the DNA. For hybridizing probes longer than about 100 nucleotides with filter-bound target DNA or RNA, one way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 42° C. (or other similar hybridization solutions, such as one containing about 50% formamide, with a hybridization temperature of about 42° C.), and washing conditions of about 60° C., in 0.5× SSC, 0.1% SDS. Conditions of high stringency can also be readily determined by the skilled artisan based on, for example, the length and base composition of the DNA. Generally, such conditions are defined as hybridization conditions as above, but with washing at approximately 68° C., 0.2×SSC, 0.1% SDS. It should be understood that the wash temperature and wash salt concentration can be adjusted as necessary to achieve a desired degree of stringency by applying the basic principles that govern hybridization reactions and duplex stability, as known to those skilled in the art (see, e.g., Sambrook et al., 1989). It should be further understood that hybridization conditions for oligonucleotide probes of defined length and sequence can be designed by applying formulae known in the art (e.g., see Sambrook et al., 1989, at 11.4511.47).

Also included as an embodiment of the invention is DNA encoding polypeptide fragments that have at least one activity of Pellino polypeptides, and DNA encoding polypeptides of at least about 16 amino acids, or of at least about 32 amino acids, which polypeptides are useful as immunogens. DNAs encoding polypeptides comprising inactivated N-glycosylation site(s), inactivated protease processing site(s), or conservative amino acid substitution(s), are also included, as described below. For example, the IL-1R-homologous domain may be useful as a dominant negative regulator of IL-1R signaling, or in an assay to identify small molecules that can inhibit or otherwise regulate IL-1 signaling.

In another embodiment, the DNA molecules of the invention also comprise polynucleotides that are at least 80% identical to a native sequence, and polynucleotide molecules that are at least 85% identical to a native molecule. Also contemplated are embodiments in which a DNA molecule is at least 90% identical, at least 95% identical, at least 98% identical, at least 99% identical, or at least 99.9% identical to a native sequence. Percent identity is defined as the number of aligned symbols, i.e. nucleotides or amino acids, which are identical, divided by the total number of symbols in the shorter of the two sequences. The degree of homology (percent identity) between two sequences may be determined by using the alignment method of Needleman and Wunsch (*J. Mol. Biol*. 48:443, 1970) as revised by Smith and Waterman (*Adv. Appl. Math* 2:482, 1981), with a unary comparison matrix (containing a value of 1 for identities and 0 for nonidentities) for nucleotides, and the weighted comparison matrix of Gribskov and Burgess (*Nucl. Acids. Res*. 14:6745, 1986) as described by Schwartz and Dayhoff (Atlas of Protein Sequence and Structure, National Biomedical Research Foundation, pp. 353–358, 1979) for amino acids. Preferably, the comparison is done using a computer program. An exemplary, preferred computer program is the Genetics Computer Group (GCG; Madison, Wis.) Wisconsin package version 10.0 program, 'GAP.' The preferred default parameters for the 'GAP' program includes: (1) The GCG implementation of the previously stated comparison matrixes for nucleotides and amino acids; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by one skilled in the art of sequence comparison may also be used.

Similarly, the DNAs of the invention include variants that differ from a native DNA sequence because of one or more deletions, insertions or substitutions, but that encode a biologically active polypeptide. In addition, DNAs that encode various additions or substitutions of amino acid residues or sequences, or deletions of terminal or internal residues or sequences are encompassed by the invention.

Examples of such DNAs include those that have been modified to facilitate expression of a polypeptide with an altered N-linked glycosylation site or KEX-2 protease site, as well as those in which codons that encode Cys residues that are not necessary for biological activity are eliminated or altered to encode another amino acid. These and other variant peptides are disclosed herein; DNAs encoding them are also encompassed by the invention.

The invention also provides isolated DNAs useful in the production of polypeptides. Such polypeptides may be prepared by any of a number of conventional techniques. A DNA sequence encoding a Pellino polypeptide, or desired fragment thereof may be subcloned into an expression vector for production of the polypeptide or fragment. The DNA sequence advantageously is fused to a sequence encoding a suitable leader or signal peptide.

The desired DNA fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-termiinus of the coding sequence.

The well-known polymerase chain reaction (PCR) procedure also may be employed to isolate and amplify a DNA encoding a desired protein or fragment thereof. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., Science 239:487 (1988); Recombinant DNA Methodology, Wu et al., eds., Academic Press, Inc., San Diego (1989), pp. 189–196; and PCR Protocols: A Guide to Methods and Applications, Innis et al., eds., Academic Press, Inc. (1990).

The present invention also provides genes corresponding to the nucleic acid sequences disclosed herein. "Corresponding genes" or "corresponding genomic nucleic acids" are the regions of the genome that are transcribed to produce the mRNAs from which cDNA nucleic acid sequences are derived and can include contiguous regions of the genome necessary for the regulated expression of such genes. Corresponding genes can therefore include but are not limited to coding sequences, 5' and 3' untranslated regions, alternatively spliced exons, introns, promoters, enhancers, and silencer or suppressor elements. Corresponding genomic nucleic acids can include 10000 basepairs (more preferably, 5000 basepairs, still more preferably, 2500 basepairs, and most preferably, 1000 basepairs) of genomic nucleic acid sequence upstream of the first nucleotide of the genomic sequence corresponding to the initiation codon of the Pellino polypeptide coding sequence, and 10000 basepairs (more preferably, 5000 basepairs, still more preferably, 2500 basepairs, and most preferably, 1000 basepairs) of genomic nucleic acid sequence downstream of the last nucleotide of the genomic sequence corresponding to the termination codon of the Pellino polypeptide coding sequence. The corresponding genes or genomic nucleic acids can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" or "an isolated genomic nucleic acid" is a genomic nucleic acid that has been separated from the adjacent genomic sequences present in the genome of the organism from which the genomic nucleic acid was isolated.

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the nucleic acid sequences set forth above. Full length polypeptides comprise an amino acid sequence as depicted in SEQ ID NOs:2, 4, and 6, with useful fragments comprising amino acids 132 to 289 of SEQ ID NOs:2 and 4, and amino acids 133 to 190 of SEQ ID NO:6. As mentioned above, the N-terminal and C-terminal amino acids of these and other fragments can vary about two amino acids from those given (i.e., the N-terminus can vary from amino acids 130 to 134 of SEQ ID NOs:2 and 4 and 131 to 135 of SEQ ID NO:6; and the C-terminus can vary from amino acids 187 to 191 of SEQ ID NOs:2 and 4 and 188 to 192 of SEQ ID NO:6).

The inventive peptides and fragments thereof may be recombinantly expressed as an intracellular polypeptide, preferably in non-mammalian cells. Such peptides may be obtained by isolating cells that express the polypeptide from the culture medium (e.g., by centrifugation or filtration), solubilizing the cells, and isolating the peptide from the solubilized cells. Choice of solubilization techniques will depend on the cells used for expression. Purification of the polypeptide from recombinant host cells is facilitated by expression of the polypeptide as a fusion protein with a tag protein as discussed herein.

The inventive peptides and fragments thereof may also be recombinantly expressed as a soluble polypeptide capable of being secreted from the cells in which it is made. Such soluble peptides may be obtained by separating intact cells that express the soluble polypeptide from the culture medium (e.g., by centrifugation or filtration), and isolating the soluble peptide from the medium (supernatant). Purification of the polypeptides from recombinant host cells is facilitated by expression of the polypeptide as a secreted protein, which can be useful in obtaining large amounts of the soluble polypeptide as a therapeutic or diagnostic agent, or for use in assays. Because the N-terminus and C-terminus of recombinantly expressed polypeptides may vary by several amino acids, including from about 1 amino acid to about 10 amino acids, the polypeptides of this invention can vary accordingly.

The inventive polypeptides thus include, but are not limited to: (a) polypeptides comprising amino acids x1 to x2, wherein x1 is any of the amino acids in positions 1 through 10 of SEQ ID NO:2, and x2 is any of the amino acids in positions 408 through 418 of SEQ ID NO:2; (b) polypeptides comprising amino acids x1 to x2, wherein x1 is any of the amino acids in positions 1 through 10 of SEQ ID NO:4, and x2 is any of the amino acids in positions 408 through 418 of SEQ ID NO:4; and (c) polypeptides comprising amino acids x1 to x2, wherein x1 is any of the amino acids in positions 1 through 10 of SEQ ID NO:6, and x2 is any of the amino acids in positions 409 through 419 of SEQ ID NO:6. Polypeptides similar to any of the foregoing may also be derived from SEQ ID NO:8.

Other embodiments include polypeptides comprising: (a) amino acids x1 to x2, wherein x1 is any of the amino acids in positions 1 through 10 of SEQ ID NO:2, and x2 is any of the amino acids in positions 187 through 191 of SEQ ID NO:2; (b) amino acids x1 to x2, wherein x1 is any of the amino acids in positions 1 through 10 of SEQ ID NO:4, and x2 is any of the amino acids in positions 187 through 191 of SEQ ID NO:4; and (c) amino acids x1 to x2, wherein x1 is any of the amino acids in positions 1 through 10 of SEQ ID NO:6, and x2 is any of the amino acids in positions 188 through 192 of SEQ ID NO:6.

The invention also comprehends polypeptides comprising: (a) amino acids x1 to x2, wherein x1 is any of the amino acids in positions 1 through 10 of SEQ ID NO:2, and x2 is any of the amino acids in positions 130 through 134 of SEQ ID NO:2; (b) amino acids x1 to x2, wherein x1 is any of the amino acids in positions 1 through 10 of SEQ ID NO:4, and x2 is any of the amino acids in positions 130 through 134 of SEQ ID NO:4; and (c) amino acids x1 to x2, wherein x1 is any of the amino acids in positions 1 through 10 of SEQ ID NO:6, and x2 is any of the amino acids in positions 129 through 133 of SEQ ID NO:6.

Additional embodiments include polypeptides comprising: (a) amino acids x1 to x2, wherein x1 is any of the amino acids in positions 130 through 134 of SEQ ID NO:2, and x2 is any of the amino acids in positions 408 through 418 of SEQ ID NO:2; (b) amino acids x1 to x2, wherein x1 is any of the amino acids in positions 130 through 134 of SEQ ID NO:4, and x2 is any of the amino acids in positions 408 through 418 of SEQ ID NO:4; and (c) amino acids x1 to x2, wherein x1 is any of the amino acids in positions 129 through 133 of SEQ ID NO:6, and x2 is any of the amino acids in positions 409 through 419 of SEQ ID NO:6.

Also included within the scope of the invention are polypeptides comprising: (a) amino acids x1 to x2, wherein x1 is any of the amino acids in positions 187 through 191 of SEQ ID NO:2, and x2 is any of the amino acids in positions 408 through 418 of SEQ ID NO:2; (b) amino acids x1 to x2, wherein x1 is any of the amino acids in positions 187 through 191 of SEQ ID NO:4, and x2 is any of the amino acids in positions 408 through 418 of SEQ ID NO:4; and (c) amino acids x1 to x2, wherein x1 is any of the amino acids in positions 188 through 192 of SEQ ID NO:6, and x2 is any of the amino acids in positions 409 through 419 of SEQ ID NO:6. Polypeptides similar to any of the foregoing may also be derived from SEQ ID NO:8.

The invention also provides Pellino polypeptides and fragments thereof that retain a desired activity. Particular embodiments are directed to polypeptide, fragments that retain the ability to bind a member of the chymotrypsin family of proteases. Such a fragment may be a soluble polypeptide, as described above. In another embodiment, the polypeptides and fragments advantageously include regions that are conserved in the Pellino family as described above.

Also provided herein are polypeptide fragments comprising at least 8, 12, 16, or at least 32, contiguous amino acids of the sequence of SEQ ID NO:2. Such polypeptide fragments may be employed as immunogens in generating antibodies, as small molecule agonists or antagonists of Pellino activity, and in various assays for Pellino activity.

Naturally occurring variants as well as derived variants of the polypeptides and fragments are provided herein. Variants may exhibit amino acid sequences that are at least 80% identical, or at least about 85% identical, to the native polypeptide disclosed herein. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined as described previously herein.

The variants of the invention include, for example, those that result from alternate mRNA splicing events or from proteolytic cleavage. Alternate splicing of mRNA may, for example, yield a truncated but biologically active protein, such as a naturally occurring, shortened form of the protein. As mentioned above, variations attributable to proteolysis include, for example, differences in the N- or C-termini upon expression in different types of host cells, due to proteolytic removal of one or more terminal amino acids from the protein (generally from about one to about five terminal amino acids) or other differences in protein expression. Proteins in which differences in amino acid sequence are attributable to genetic polymorphism (allelic variation among individuals producing the protein) are also contemplated herein.

Other variants include fusion proteins, such as those prepared by expression in recombinant culture as N-terminal or C-terminal fusions. Examples of fusion proteins include fusion proteins that will form oligomers, such as a Pellino/Fc fusion protein (for example, as described in U.S. Pat. No. 5,962,406, issued Oct. 5, 1999), or a zipper fusion protein (U.S. Pat. No. 5,716,805, issued Feb. 10, 1998). Further, fusion proteins can comprise peptides added to facilitate purification and identification (often referred to as tag proteins). Such peptides include, for example, poly-His or the antigenic identification peptides described in U.S. Pat. No. 5,011,912 and in Hopp et al., *Bio/Technology* 6:1204, 1988. Additional, useful tag proteins include green fluorescent protein (GFP; Chalfie et al., *Science* 263:802, 1994), an N-terminal peptide that contains recognition sites for a monoclonal antibody, a specific endopeptidase, and a site-specific protein kinase (PKA; Blanar and Rutter, *Science* 256:1014, 1992), birA (Altman et al., *Science* 274:94, 1996) .and glutathione S transferase (GST: Smith and Johnson, *Gene* 67:31, 1988).

One such tag peptide is the FLAG peptide, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG peptide are available from Eastman Kodak Co., Scientific Imaging Systems Division, New Haven, Conn.

Another useful tag peptide is the GST peptide, which binds glutathione, also facilitating purification of expressed recombinant protein. Recombinant protein can be purified by affinity chromatography using a suitable chromatography matrix to which has been attached glutathione, as described in Smith and Johnson, supra, hereby incorporated by reference. Suitable chromatography matrixes include Glutathione-Agarose beads (Pharmacia). Recombinant protein can be eluted with an excess of glutathione. Alternatively, a specific enzymatic cleavage site (such as a thrombin cleavage site) can be included n the recombinant fusion protein, and the desired polypeptide removed from the affinity matrix by treatment with the enzyme that cleaves the fusion protein at the cleavage site.

Among the variant polypeptides provided herein are variants of native polypeptides that retain the native biological activity or the substantial equivalent thereof. One example is a variant that binds a binding partner with essentially the same binding affinity as does the native form. Binding affinity can be measured by conventional procedures, e.g., as described in U.S. Pat. No. 5,512,457 and as set forth below. Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence. A given amino acid may be replaced, for example, by a residue having similar physiochemical characteristics. Examples of such physiochemically conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other substitutions, e.g., involving substitutions of entire regions having similar hydrophobicity characteristics, are well known.

The invention further includes polypeptides of the invention with or without associated native-pattern glycosylation. Polypeptides expressed in yeast or mammalian expression systems (e.g., CHO or COS-7 cells) can be similar to or significantly different from a native polypeptide in molecular weight and glycosylation pattern, depending upon the choice of expression system. Further, a given preparation may include multiple differentially glycosylated species of the protein. Expression of polypeptides of the invention in bacterial expression systems, such as E. coli, provides non-glycosylated molecules. Glycosyl groups can also be removed through conventional chemical or enzymatic methods, in particular those utilizing glycopeptidase. In general, glycosylated polypeptides of the invention can be incubated with a molar excess of glycopeptidase (Boehringer Mannheim). Recombinant technology can also be applied to reduce glycosylation that occurs in eukaryotic expression systems, for example, as described in U.S. Pat. No. 5,071,972 and EP 276,846, hereby incorporated by reference. Other variants are prepared by modification of adjacent dibasic amino acid residues, to enhance expression in yeast systems in which KEX2 protease activity is present, as disclosed in EP 212,914. In another example of variants, sequences encoding Cys residues that are not essential for biological activity can be altered to cause the Cys residues to be deleted or replaced with other amino acids, as disclosed in U.S. Pat. No. 5,962,406, issued Oct. 5, 1999.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Production of Polypeptides and Fragments Thereof

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that procedures for producing and purifying the expressed polypeptides will vary according to such factors as the type of host cells employed, and whether the polypeptide is membrane-bound or a soluble polypeptide that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. An origin of replication that confers the ability to replicate in the desired host cells, and a selection gene by which transformants are identified, are generally incorporated into the expression vector. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. Accordingly, a protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Appropriate cloning and expression vectors for use with bacterial, fungal, yeast, and mammalian cellular hosts are described, for example, in Pouwels et al. Cloning Vectors: A Laboratory Manual, Elsevier, N.Y., (1985). Cell-free translation systems could also be employed to produce polypeptides using RNAs derived from DNA constructs disclosed herein.

Mammalian or insect host cell culture systems also may be employed to express recombinant polypeptides. Bacculovirus systems for production of heterologous proteins in insect cells are reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CVI (ATCC CCL 70) as described by McMahan et al. (EMBO J. 10: 2821, 1991).

A commonly used cell line is dihydrofolate reductase (DHFR)– CHO cells which are auxotrophic for glycine, thymidine and hypoxanthine, and can be transformed to the DHFR+ phenotype using DHFR cDNA as an amplifiable dominant marker. One such DHFR– CHO cell line, DXB11, was described by Urlaub and Chasin (Proc. Natl. Acad. Sci. USA 77:4216, 1980). Another exemplary DHFR– CHO cell line is DG44 (see, for example, Kaufman, R. J., Meth. Enzymology 185:537 (1988). Other cell lines developed for specific selection or amplification schemes will also be useful with the invention.

Several transfection protocols are known in the art, and are reviewed in Kaufman, R. J., supra. The transfection protocol chosen will depend on the host cell type and the nature of the gene of interest, and can be chosen based upon routine experimentation. The basic requirements of any such protocol are first to introduce DNA encoding the protein of interest into a suitable host cell, and then to identify and isolate host cells which have incorporated the heterologous DNA in a stable, expressible manner. Other useful transfection protocols are discussed in U.S. Pat. No. 6,027,915, issued Feb. 22, 2000. Transfection of cells with heterologous DNA and selection for cells that have taken up the heterologous DNA and express the selectable marker results in a pool of transfected cells. Individual cells in these pools will vary in the amount of DNA incorporated and in the chromosomal location of the transfected DNA. To generate stable cell lines, individual cells can be isolated from the pools and cultured (a process referred to as cloning).

A method of amplifying the gene of interest is also desirable for expression of the recombinant protein, and typically involves the use of a selection marker (reviewed in Kaufman, R. J., supra). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifiable markers are suitable for use in the inventive expression vectors (for example, as described in Maniatis, Molecular Biology: A Laboratory Manual, Cold Spring Harbor Laboratory, NY, 1989; pgs 16.9–16.14).

Useful selectable markers for gene amplification in drug-resistant mammalian cells are shown in Table 1 of Kaufman, R. J., supra (1988), and include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin. Other dominant selectable markers are discussed in U.S. Pat. No. 6,027,915, issued Feb. 22, 2000).

Useful regulatory elements, described previously, can also be included in the plasmids or expression vectors used to transfect mammalian cells. The transfection protocol chosen, and the elements selected for use therein, will depend on the type of host cell used. Those of skill in the art are aware of numerous different protocols and host cells, and can select an appropriate system for expression of a desired protein, based on the requirements of their selected cell culture system(s).

A useful high expression vector, pCAVNOT, has been described by Mosley et al., Cell 59:335–348, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG and pDC311, can also be used. FLAG technology is centered on the fusion of a low molecular weight (ikD), hydrophilic, FLAG marker peptide to the N-terminus of a recombinant protein expressed by pFLAG expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

A signal peptide may be employed to facilitate secretion of the protein, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367, 566; the type I interleukin-1 receptor signal peptide described in U.S. Pat. No. 4,968,607; and the type II interleukin-1 receptor signal peptide described in EP 460, 846.

Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other cellular components, such as unrelated proteins or polypeptides, lipids and DNA or RNA, for example, as a purification product of recombinant expression systems such as those described above or as a purified product from a non-recombinant source such as naturally occurring cells and/or tissues.

In one embodiment, the purification of recombinant polypeptides or fragments can be accomplished by expressing the inventive polypeptide(s) as a fusion protein with a peptide (often referred to as a tag peptide) for which an affinity purification scheme is known in the art. Such fusion partners can include the poly-His or other tag peptides described above as well as an Fc moiety or a zipper moiety.

With respect to purification, as is known to the skilled artisan, procedures for purifying a recombinant polypeptide or fragment will vary according to such factors as the type of host cells employed and whether or not the recombinant polypeptide or fragment is secreted into the culture medium. In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps.

As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification.

Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns.

Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. In this aspect of the invention, binding proteins, such as antibodies against Pellino or other molecules that bind Pellino can be bound to a solid phase support such as a column chromatography matrix or a similar substrate suitable for identifying, separating, or purifying Pellino. Adherence of Pellino to a solid phase contacting surface can be accomplished by any means, for example, magnetic microspheres can be coated with Pellino binding proteins (or other Pellino-binding molecules) and held in the incubation vessel through a magnetic field.

Solutions containing Pellino polypeptides are contacted with the solid phase under conditions promoting binding of Pellino polypeptides to the binding partner; unbound material is then washed away. Methods of releasing positively selected peptides from the solid phase are known in the art and encompass, for example, use of a high salt elution buffer followed by dialysis into a lower salt buffer, or by changing pH (or other characteristics depending on the affinity matrix utilized), or competitive removal using a naturally occurring substrate of the affinity moiety. The methods are preferably non-injurious to the Pellino polypeptides.

In one exemplary method, solutions containing Pellino polypeptides of the invention first can be incubated with a biotinylated Pellino binding partner. Incubation periods are typically at least one hour in duration to ensure sufficient binding to polypeptides of the invention. The resulting mixture then is passed through a column packed with avidin-coated beads, whereby the high affinity of biotin for avidin provides the binding of the Pellino polypeptides to the beads. Use of avidin-coated beads is known in the art. See Berenson, et al. J. Cell. Biochem., 10D:239 (1986). Washing of unbound material and the release of the bound cells are performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Uses of Pellino Nucleic Acid or Oligonucleotides

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of Pellino proteins from other mammalian species are contemplated herein, probes based on the DNA sequence of SEQ ID NOs:1, 3, 5, 7, or 11 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

All or a portion of the nucleic acids of SEQ ID NOs:1, 3, 5, 7, or 11, including oligonucleotides, can be used by those skilled in the art using well-known techniques to identify the human chromosome, and the specific locus thereof, that contains the DNA of a Pellino family member. Useful techniques include, but are not limited to, using the sequence or portions, including oligonucleotides, as a probe in various wellknown techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization, using primers that lie within a putative exon of the gene of interest and which amplify a product from human genomic DNA, but do not amplify genomic DNA from other species. The results of the PCR are converted into a data vector that is scored and the chromosomal assignment and placement relative to known Sequence Tag Site (STS) markers on the radiation hybrid map is determined. Human Pellino-1 maps to chromosome 2, places 7.15 cR from WI-6130.

The nucleic acid of SEQ ID NOs 1, 3, 5, 7, or 11, or a fragment thereof can be used by one skilled in the art using well-known techniques to analyze abnormalities associated with gene mapping to a chromosome that comprises a gene encoding Pellino. This enables one to distinguish conditions in which this marker is rearranged or deleted. In addition, nucleotides of SEQ ID NOs:1, 3, 5, 7, or 11, or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement or supplementation thereof with normal genes, by various gene therapy techniques that are known in the art. Defective genes may be detected in in vitro diagnostic assays, and by comparison of a native nucleotide sequence disclosed herein with that of a gene derived from a person suspected of harboring a defect in this gene.

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA of SEQ ID NOs:1, 3, 5, 7, or 11. Such a fragment generally comprises at least about 17 nucleotides, preferably from about 17 to about 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988). Binding of antisense or sense oligonucleotides to target nucleic acid sequences results in the formation of complexes that block or inhibit protein expression by one of several means, as discussed in U.S. Pat. No. 5,783,665, issued Jul. 21, 1998. Organic moieties and other moieties that increases affinity of the oligonucleotide for a target nucleic acid sequence, or intercalating agents, may be attached to sense or antisense oligonucleotides to modify binding specificities of the antisense or sense oligonucleotide for the target nucleotide sequence. The antisense or sense oligonucleotides may be introduced into a cell containing the target nucleic acid sequence by any gene transfer method, including, for example, lipofection, CaPO4-mediated DNA transfection, electroporation, or by using gene transfer vectors such as Epstein-Barr virus. Sense or antisense oligonucleotides also may be introduced into a cell containing the target nucleotide sequence by formation of a conjugate with a ligand binding molecule, as described in WO 91/04753. Alternatively, a sense or an antisense oligonucleotide may be introduced into a cell containing the target nucleic acid sequence by formation of an oligonucleotide-lipid complex, as described in WO 90/10448.

The inventive DNAs will also be useful in the development of transgenic and/or knockout cells and animals. Those of ordinary skill in the art are aware of various methods by which such cells or animals can be prepared; an exemplary method is given in U.S. Pat. No. 5,565,321, issued Oct. 15, 1996. The techniques described therein can be used with the inventive sequences by the application of routine experimentation.

Uses of Pellino Polypeptides

Because Pellino proteins are homologous to the Pellino proteins of Drosophila, an important molecule in the signaling cascade for the IL-1R/Toll family of receptors, small molecule inhibitors of its function or protein associations(or antisense or other inhibitors of its synthesis) may be useful in treating autoimmune andlor inflammatory disorders. Accordingly, the Pellino polypeptides of the present invention may be used in a screening assay to identify compounds and small molecules which inhibit (antagonize) or enhance (agonize) activation of the polypeptides of the instant invention.

Thus, for example, polypeptides of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the instant invention may include small molecules, peptides and antibodies that bind to and occupy a binding site of the inventive polypeptides or a binding partner thereof, causing them to be unavailable to bind to their natural binding partners and therefore preventing normal biological activity. Potential agonists include small molecules, peptides and antibodies which bind to the instant polypeptides or binding partners thereof, and elicit the same or enhanced biologic effects as those caused by the binding of the polypeptides of the instant invention.

Small molecule agonists and antagonists are usually less than 10K molecular weight and may possess a number of physicochemical and pharmacological properties which enhance cell penetration, resist degradation and prolong their physiological half-lives (Gibbs, J., Pharmaceutical Research in Molecular Oncology, Cell, Vol. 79 (1994)). Antibodies, which include intact molecules as well as fragments such as Fab and F(ab')2 fragments, as well as recombinant molecules derived therefrom, may be used to bind to and inhibit the polypeptides of the instant invention by blocking the propagation of a signaling cascade. It is preferable that the antibodies are humanized, and more preferable that the antibodies are human. The antibodies of the present invention may be prepared by any of a variety of well-known methods.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays.

Homogeneous assays are "mix and read" assays that are very amenable to robotic application, whereas heterogeneous assays require separation of bound analyte from free by more complex unit operations such as filtration, centrifugation or washing. These assays are utilized to detect a wide variety of specific biomolecular interactions and the inhibition thereof by small organic molecules, including protein-protein, receptor-ligand, enzyme-substrate, etc. These assay methods and techniques are well known in the art and are described more fully in the following: High Throughput Screening: The Discovery of Bioactive Substances, John P. Devlin (ed.), Marcel Dekker, New York, 1997, ISBN: 0-8247-0067-8; and the internet sites of lab-robotics.org and sbsonline.org. The screening assays of the present invention are amenable to high throughput screening of chemical libraries and are suitable for the identification of small molecule drug candidates, antibodies, peptides and other antagonists and/or agonists.

One embodiment of a method for identifying molecules which inhibit or antagonize the polypeptides involves adding a candidate molecule to a medium which contains cells that express the polypeptides of the instant invention; changing the conditions of said medium so that, but for the presence of the candidate molecule, the polypeptides would be bound to their natural ligands, substrates or effector molecules, and observing the binding and stimulation or inhibition of a functional response. The activity of the cells which were contacted with the candidate molecule may then be compared with the identical cells which were not contacted and antagonists and agonists of the polypeptides of the instant invention may be identified. The measurement of biological activity may be performed by a number of well-known methods such as measuring the amount of protein present (e.g. an ELISA) or of the proteins activity. A decrease in biological stimulation or activation would indicate an antagonist. An increase would indicate an agonist.

Screening assays can further be designed to find molecules that mimic the biological activity of the polypeptides of the instant invention. Molecules which mimic the biological activity of a polypeptide may be useful for enhancing the biological activity of the peptide. To identify compounds for therapeutically active agents that mimic the biological activity of a polypeptide, it must first be determined whether a candidate molecule binds to the polypeptide. A binding candidate molecule is then added to a biological assay to determine its biological effects. The biological effects of the candidate molecule are then compared to those of the polypeptide(s).

Another embodiment of the invention relates to uses of Pellino polypeptides to study cell signal transduction. Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Accordingly, these novel Pellino polypeptides can be used as reagents to identify novel molecules involved in signal transduction pathways.

The inventive polypeptides are involved in IL-1 signaling, and as such can be used as inhibitors of the IL-1 signaling pathway. Accordingly, they find utility in in vitro screening assays and in vivo therapeutics. As therapeutics that are cell membrane permeable, the Pellino polypeptides and fragments thereof can be administered to agonize or antagonize IL-1R mediated signaling pathways, thus providing useful immunoregulators. Various liposome-based compositions of the inventive polypeptides are envisioned herein.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble Pellino polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury (for example, intracoronary or intra tumor administration or injection into a joint undergoing an inflammatory reaction). Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

The polypeptide of the instant invention may also be administered by the method of protein transduction. In this method, the Pellino polypeptide is covalently linked to a protein-transduction domain (PTD) such as, but not limited to, TAT, Antp, or VP22 (Schwarze et al., 2000, *Cell Biology* 10: 290–295). The PTD-linked Pellino polypeptides can then be transduced into cells by adding them to tissue-culture media containing the cells (Schwarze et al., 1999, *Science* 285: 1569; Lindgren et al., 2000, *TiPS* 21: 99; Derossi et al., 1998, *Cell Biology* 8: 84; WO 00/34308; WO 99/29721; and WO 99/10376). Moreover, it has been found that DNA encoding a polypeptide can be administered to a mammal in such a way that it is taken up by cells, and expressed. The resultant protein will then be available to exert a therapeutic effect. Accordingly, compositions comprising nucleic acids in physiologically acceptable formulations are also contemplated. DNA may be formulated for injection, for example.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a DNA encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (*Proc. Natl. Acad. Sci. USA* 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

The following examples are provided to further illustrate particular embodiments of the invention, and are not to be construed as limiting the scope of the present invention.

EXAMPLE 1

Identification of Pellino Nucleic Acid and Polypeptide Sequences

The polynucleotide sequences of ESTs isolated from murine dendritic cells identified two clones containing open reading frames with a high degree of similarity to the *Drosophila* protein Pellino (Grosshans et al., supra). Appropriate flanking PCR primers were designed, and a novel nucleic acid was amplified from a murine cDNA library and cloned; the nucleotide sequence and encoded amino acid sequence of this clone, which is called Pellino-1 (previously referred to as Conserved Inflammatory Signal Target-1), are shown in SEQ ID NO:1 and SEQ ID NO:2, respectively. Human sequences from the high-throughput genomic (HTG) and EST divisions of the public GenBank database were compared with murine Pellino-1, and an open reading frame for the human Pellino-1 homolog was assembled. PCR primers were designed based upon this human sequence, and a cDNA clone was isolated by PCR amplification from a human dermal fibroblast cDNA library. The nucleotide and amino acid sequence of this protein are shown in SEQ ID NO:3 and SEQ ID NO:4, respectively. Subsequently, Rich et al. published the coding and amino acid sequences of "human Pellino" (GenBank Accession Numbers AJ278859 and CAC04320, 23 August 2000); the amino acid sequence of the "human Pellino" polypeptide is identical to that of human Pellino-1 (SEQ ID NO:4) except for a Ser to Phe substitution at position 11. The difference between the human Pellino and SEQ ID NO:4 amino acid sequences may represent a naturally occurring allelic variation between nucleic acids encoding these amino acid sequences within the human population. Partial Pellino-1 amino acid sequences have also been published in WO 2000/58350; EP 1 074 617; and WO 2001/09318.

By querying public EST databases, a portion of a second, related gene, referred to as Pellino-2, was identified in the mouse and human. Pellino-2 amino acid sequences are 80% identical to their respective Pellino-1 counterparts. Appropriate primers were designed, and murine Pellino-2 DNA was cloned substantially as described for Pellino-1; the nucleotide and amino acid sequence of murine Pellino-2 is shown in SEQ ID NO:5 and SEQ ID NO:6, respectively. The predicted nucleotide and amino acid sequence of human Pellino-2 is shown in SEQ ID NOs:7 and 8.

A data set was received from Celera Genomics (Rockville, Md.) containing a listing of amino acid sequences predicted to be encoded by the human genome. This data set was searched with a BLAST algorithm to identify Pellino polypeptide sequences and several partial amino acid sequences were found that appeared to be related to a new human Pellino polypeptide, Pellino-3. Comparison of these partial Pellino-3 amino acid sequences to genomic and cDNA sequences allowed the predicted human Pellino-3 nucleotide and amino acid sequences, SEQ ID NO:11 and SEQ ID NO:12, respectively, to be assembled. Two possible allelic variations have been detected within the human Pellino-3 amino acid sequence (SEQ ID NO:12): a deletion of the Leu residue at position 96, and an Arg to Ala substitution at residue 353.

The amino acid sequences of murine ("Mm") and human ("Hs") Pellino-1 and Pellino-2 polypeptides, and human Pellino-3 polypeptide (SEQ ID NO:2, SEQ ID NO:4, SEQ ID NO:6, SEQ ID NO:8, and SEQ ID NO:12) were compared with the amino acid sequences of Pellino-related Pellino polypeptides from other species (*Drosophila melanogaster*, "Dm", SEQ ID NO:13; *Ciona intestinalis*, "Ci", SEQ ID NO:14; and *Caenorhabditis elegans*, "Ce", SEQ ID NO:15) using the GCG "pretty" multiple sequence alignment program, with amino acid similarity scoring matrix=blosum62, gap creation penalty=8, and gap extension penalty=2. The alignment of these sequences is shown in Table 1, and indicates consensus amino acid residues which are identical among at least three of the amino acid sequences in the alignment. The capitalized residues in the alignment are those which match the consensus residues. Pellino-1 and -2 share 82% identity at the amino acid level, and the degree of conservation between human and mouse is extremely high; only one amino acid is different between human and mouse Pellino-1, and Pellino-2 is 95% conserved between these species. The predicted Pellino-3 amino acid sequence is 70% and 71% identical to human Pellino-1 and -2, respectively. There is a surprising degree of similarity between human Pellino-1, for example, and the homologous protein from *C. elegans* (SEQ ID NO:15), which share 44% amino acid identity and 53% amino acid similarity. It is evident from a cursory inspection of the alignment that sequence conservation is not concentrated in any particular part of the Pellino protein, but extends throughout. This, and the fact that all the Pellino polypeptides (except for *Drosophila* Pellino and human Pellino-3, which contain small N-terminal extensions) are of a very similar size, suggest that (1) all parts of the protein are involved in its wild-type function and (2) few or no amino acids extraneous to that wild-type function exist in the polypeptides. There is a particularly well-conserved central domain, extending from amino acid 132 through amino acid 193 in Pellino-1 (SEQ ID NOs 2 and 4; which corresponds to amino acids 134 through 195 in SEQ ID NO:8 and amino acids 158 through 219 in SEQ ID NO:12), and an absolutely conserved motif from residue 245 through residue 254 of SEQ ID NOs 2 and 4 (which corresponds to amino acids 247 through 256 in SEQ ID NO:8 and amino acids 271 through 280 in SEQ ID NO:12). The C-terminal portions of Pellino polypeptides are interspersed by a series of short, invariant motifs, in which cysteine, proline, histidine and large hydrophobic residues are prevalent. The arrangement of some of the conserved sequences, including a Cys-Gly-His triplet and two Cys-Pro-X-Cys motifs, is reminiscent of the structure of the C3HC4 RING-finger subfamily of Zinc-finger domains, which mediate protein-protein and protein-DNA interactions in a diverse group of proteins, including tumor suppressors, proto-oncogenes, and signaling molecules including the TRAFs, with specific examples of polypeptides containing similar RING-finger domains including human ring finger protein-1 (hRING1, GenBank NP_002922); chicken ring finger protein (C-RZF, GenBank 1589724); human proto-oncogene CBL (hC-CBL, GenBank P22681); murine TNFR2-TRAF signaling complex protein (mc-IAP1, GenBank AAC42078); human TRAF-interacting protein (hTRIP, GenBank NP_005870); human TNF receptor-associated factor 3 (hTRAF3, GenBank NP_003291); human TNF receptor-associated factor 2 (hTRAF2, GenBank NP_066961); and *Drosophila* neuralized protein (neu, GenBank S35371). The Pellino RING-finger-like domains comprise the following amino acid sequences: amino acid 333 through amino acid 398 of SEQ ID NOs 2 and 4; amino acids 335 through 400 in SEQ ID NO:8 and the corresponding region of SEQ ID NO:6; and amino acids 360 through 425 in SEQ ID NO:12. There are conserved cysteine residues within the Pellino polypeptide RING-finger-like domains, located at positions 333, 336, 367, 371, 395, and 398 of SEQ ID NOs 2 and 4 (and at positions 335, 338, 369, 373, 397, and 400 of SEQ ID NO:8 and the corresponding positions in SEQ ID NO:6, and at positions 360, 363, 394, 398, 422, and 425 of SEQ ID NO:12). In Pellino polypeptides the conserved cysteine and histidine residues are more widely separated than would be typical for a classical RING-finger domain, in which the intervening sequences form the finger-like loops. The first cysteine following the conserved histidine of the canonical RING-finger domain is missing in Pellino, but we note that there is an almost invariant histidine at position 362 of SEQ ID NOs 2 and 4 (and at position 364 of SEQ ID NO:8 and the corresponding position in SEQ ID NO:6, and at positions 389 of SEQ ID NO:12) which might be available for co-ordination to a metal ion. A second, invariant Cys-Gly-His triplet at residues 311–313 of SEQ ID NOs 2 and 4 (and at amino acids 313 through 315 of SEQ ID NO:8 and the corresponding residues in SEQ ID NO:6, and at amino acids 338 through 340 of SEQ ID NO:12) extends the zinc-finger resemblance further toward the N-terminus. Therefore, the C-terminal region of Pellino polypeptides appears to contain a novel type of Zinc finger-like domain.

Regions of amino acid similarity have also been identified between Pellino polypeptides and an insect pox virus gene, *Melanoplus sanguinipes* Entomopoxvirus (MsEPV) ORF244, which is believed to play a role in circumventing host immune defenses by blocking host defensive protein interactions (Rich et al., 2000, Immunogenetics 52: 145–149).

Amino acid substitutions and other alterations (deletions, insertions, etc.) to the Pellino amino acid sequences (SEQ ID NO:2, SEQ ID NO:4, SEQ ID NO:6, SEQ ID NO:8, and SEQ ID NO:12) are predicted to be more likely to alter or disrupt Pellino polypeptide activities if they result in changes to the capitalized residues of the amino acid sequences as shown in Table 1, and particularly if those changes do not substitute a residue present in other Pellino polypeptides at that position in the alignment shown in Table 1. Conversely, if a change is made to the Pellino amino acid sequence resulting in substitution of one or more Table 1 consensus sequence residue(s) for the Pellino residue(s) at those positions, it is less likely that such an alteration will affect Pellino polypeptide function. Embodiments of the invention include Pellino polypeptides and fragments of Pellino polypeptides comprising altered amino acid sequences. Altered Pellino polypeptide sequences share at least 30%, or more preferably at least 40%, or more preferably at least 50%, or more preferably at least 55%, or more preferably at least 60%, or more preferably at least 65%, or more preferably at least 70%, or more preferably at least 75%, or more preferably at least 80%, or more preferably at least 85%, or more preferably at least 90%, or more preferably at least 95%, or more preferably at least 97.5%, or more preferably at least 99%, or most preferably at least 99.5% amino acid identity with the Pellino amino acid sequences of SEQ ID NO:2, SEQ ID NO:4, SEQ ID NO:6, SEQ ID NO:8, and SEQ ID NO:12.

TABLE 1

Amino Acid Sequence Comparison between Pellino Polypeptides from Different Species

|  | SEQ ID NO: | 1 | | | | 50 |
|---|---|---|---|---|---|---|
| Hs Pellino-1 | 4 | ~~~~~~~~~~ | ~~~~~~~~~~ | ~~~~~~~~~~ | ~MFSPdQEnH | ..PsKaPVKY |
| Mm Pellino-1 | 2 | ~~~~~~~~~~ | ~~~~~~~~~~ | ~~~~~~~~~~ | ~MFSPdQEnH | ..PsKaPVKY |
| Hs Pellino-2 | 8 | ~~~~~~~~~~ | ~~~~~~~~~~ | ~~~~~~~~~~ | ~MFSPGQEeH | cAPnKEPVKY |
| Mm Pellino-2 | 6 | ~~~~~~~~~~ | ~~~~~~~~~~ | ~~~~~~~~~~ | ~MFSPGQEeP | sAPnKEPVKY |
| Hs Pellino-3 | 12 | ~~~~mvlegn | pevgsprtsd | lqhrgnkgsc | vlsSPGed.. | agPgeEPiKY |
| Dm Pellino | 13 | ~~~~~~~~~~ | ~~~~~~~~~m | vkrtdgtesp | ilaedGgdgH | dkPr...lrY |
| Ci Pellino | 14 | mkqegmdvsa | spalavaggm | pmdiqfeaga | syhnfsQEda | pkedegdiiY |
| Ce Pellino | 15 | ~~~~~~~~~~ | ~~~~~~~~~~ | ~mvdeselen | gtpSPpaysn | eAildddi.Y |
| consensus |  | ---------- | ---------- | ---------- | -MFSPGQE-H | -AP-KEPVKY |
|  |  | 51 | | | | 100 |
| Hs Pellino-1 | 4 | GELIVLGYNG | sLPNGDRGRR | .KSRFALfKR | PKANGVKPST | VHIacTPQA. |
| Mm Pellino-1 | 2 | GELIVLGYNG | sLPNGDRGRR | .KSRFALfKR | PKANGVKPST | VHIacTPQA. |
| Hs Pellino-2 | 8 | GELvVLGYNG | aLPNGDRGRR | .KSRFALyKR | PKANGVKPST | VHviSTPQA. |
| Mm Pellino-2 | 6 | GELvVLGYNG | aLPNGDRGRR | .KSRFALyKR | tyAsGVKPST | iHmVSTPQA. |
| Hs Pellino-3 | 12 | GELIVLGYNG | cLasGDkGRR | .rSRlALsrR | shANGVKPdv | mHhiSTPlv. |
| Dm Pellino | 13 | GELviLGYNG | yLPqGDRGRR | .rSkFvLhKR | teAsGVKrSk | hyIVqsPQt. |
| Ci Pellino | 14 | GqLIVLGtNG | qLPtGDkGRR | .rScFtLrrk | rKAtGVKPSd | qHqVyqkash |
| Ce Pellino | 15 | GELIlLGfNG | qaeNratskR | yltekvLrrR | dsANGiKkcT | VHnVST..sd |
| consensus |  | GELIVLGYNG | -LPNGDRGRR | -KSRFAL-KR | PKANGVKPST | VHIVSTPQA- |
|  |  | 101 | | | | 150 |
| Hs Pellino-1 | 4 | aKAISNKdQH | SISYTLSRaQ | TVVVEYTHDS | nTDMFQIGRS | TESPIDFVVT |
| Mm Pellino-1 | 2 | aKAISNKdQH | SISYTLSRaQ | TVVVEYTHDS | nTDMFQIGRS | TESPIDFVVT |
| Hs Pellino-2 | 8 | SKAIScKgQH | SISYTLSRnQ | TVVVEYTHDk | dTDMFQvGRS | TESPIDFVVT |
| Mm Pellino-2 | 6 | SKAISsrghH | SISYTLSReQ | TVVVEYTHDk | dTDMFQvGRS | TESPIDFVVT |
| Hs Pellino-3 | 12 | SKAlSNrgQH | SISYTLSRsh | sViVEYTHDS | dTDMFQIGRS | TEnmIDFVVT |
| Dm Pellino | 13 | SKAIldanQH | SISYTLSRnQ | aViVEYkeDt | eTDMFQvGRS | sESPIDFVVm |
| Ci Pellino | 14 | SetflsKdhH | SvSYTLpRs. | vVVVpYvHDd | nsDMFQIGRS | TEePIDFVlm |
| Ce Pellino | 15 | tKltkdKarH | tvSfhsdsnk | sVViEYaaDp | skDMFQIGRa | sddqIDFtVi |
| consensus |  | SKAISNK-QH | SISYTLSR-Q | TVVVEYTHDS | -TDMFQIGRS | TESPIDFVVT |
|  |  | 151 | | | | 200 |
| Hs Pellino-1 | 4 | DT....VPGS | ....QsnsDt | QSvQ.....S | TISRFACRIi | CeRNpPfTAR |
| Mm Pellino-1 | 2 | DT....VPGS | ....QsnsDt | QSvQ.....S | TISRFACRIi | CeRspPfTAR |
| Hs Pellino-2 | 8 | DT....isGS | ....Qntdea | QitQ.....S | TISRFACRIv | CDRNePYTAR |
| Mm Pellino-2 | 6 | DT....VsGg | ....Qned.a | QitQ.....S | TISRFACRIv | CDRNePYTAR |
| Hs Pellino-3 | 12 | DT....sPGg | .....gaaeg | pSaQ.....S | TISRyACRIl | CDRrpPYTAR |
| Dm Pellino | 13 | DT....lPGd | ....kk..Da | kvmQ.....S | TISRFACRIl | vnRcePakAR |
| Ci Pellino | 14 | Di....eaGS | siptnhkpqt | QpkQ.....S | TISRFACRIv | CDRehPYTSR |
| Ce Pellino | 15 | DTwmflpehS | daavparpqi | dvlekgdrtS | TISRFACRIl | iDRensnkAy |
| consensus |  | DT----VPGS | ----Q---D- | QS-Q-----S | TISRFACRI- | CDRN-PYTAR |
|  |  | 201 | | | | 250 |
| Hs Pellino-1 | 4 | IYAAGFDSSK | NIFLGEKAAK | WKT.sDGg.. | MDGLTTNGVL | VMHPRnGFT. |
| Mm Pellino-1 | 2 | IYAAGFDSSK | NIFLGEKAAK | WKT.sDGg.. | MDGLTTNGVL | VMHPRnGFT. |
| Hs Pellino-2 | 8 | IfAAGFDSSK | NIFLGvKAAK | WKn.pDGh.. | MDGLTTNGVL | VMHPRGGFT. |
| Mm Pellino-2 | 6 | IfAAGFDSSK | NIFLGEKAAK | WRn.pDGh.. | MDGLTTNGVL | VMHPqGGFT. |
| Hs Pellino-3 | 12 | IYAAGFDaSs | NIFLGErAAK | WrT.pDGl.. | MDGLTTNGVL | VMHPaGGFs. |
| Dm Pellino | 13 | IfAAGFDSSr | NIFLGEKAtK | Wqd..nve.. | iDGLTTNGVL | iMHPkGsFcg |
| Ci Pellino | 14 | IYAAGFDtSm | NIiLGEKApK | WtTeqnGkki | iDGLTTNGVL | iMqPknGFs. |
| Ce Pellino | 15 | lYAAGFDahq | NIsinkKslK | W.TksnGE.. | vDGLTTNGVL | llHPnkddll |
| consensus |  | IYAAGFDSSK | NIFLGEKAAK | WKT--DG--- | MDGLTTNGVL | VMHPRGGFT- |
|  |  | 251 | | | | 300 |
| Hs Pellino-1 | 4 | EDS..KPGi. | WREISVCGnV | fsLRETRSAQ | QRGKmVEiET | NqLQDGSLID |
| Mm Pellino-1 | 2 | EDS..KPGi. | WREISVCGnV | fsLRETRSAQ | QRGKmVEiET | NqLQDGSLID |
| Hs Pellino-2 | 8 | EeS..qPGV. | WREISVCGdV | YtLRETRSAQ | QRGKLVEsET | NVLQDGSLID |

TABLE 1-continued

Amino Acid Sequence Comparison between Pellino Polypeptides
from Different Species

|  | SEQ ID NO: | | | | |
|---|---|---|---|---|---|
| Mm Pellino-2 | 6 | EeS..qPGV. | WREISVCGdV | YtLRETRSAQ | QRGKLVEsET | NVLQDGSLID |
| Hs Pellino-3 | 12 | EDS..aPGV. | WREISVCGnV | YtLRdsRSAQ | QRGKLVEnEs | NVLQDGSLID |
| Dm Pellino | 13 | gna..KcGl. | WREcSVgGdV | fsLREsRSAQ | QkGqpiydEc | NiLQDGtLID |
| Ci Pellino | 14 | EsS..tPtq. | WkEtSVCGni | YqLREsRSAQ | lpGirmpedn | NVLvnGtLID |
| Ce Pellino | 15 | dDtvdKPmyk | WREvSinGdV | YepRvTRSss | akGvfVpewT | NmLQDGtLID |
| consensus |  | EDS--KPGV- | WREISVCG-V | Y-LRETRSAQ | QRGKLVE-ET | NVLQDGSLID |

|  |  | 301 | | | | 350 |
|---|---|---|---|---|---|---|
| Hs Pellino-1 | 4 | LCGATLLWRT | AeGLsHTPTv | KHLEALRQEI | NAARPQCPVG | fNTLAFPSmk |
| Mm Pellino-1 | 2 | LCGATLLWRT | AeGLsHTPTv | KHLEALRQEI | NAARPQCPVG | fNTLAFPSmk |
| Hs Pellino-2 | 8 | LCGATLLWRT | AdGLfHTPTq | KHiEALRQEI | NAARPQCPVG | LNTLAFPSin |
| Mm Pellino-2 | 6 | LCGATLLWRT | AdGLfHaPTq | KHiEALRQEI | NAARPQCPVG | LNTLAFPSin |
| Hs Pellino-3 | 12 | LCGATLLWRT | paGLlraPTl | KqLEAqRQEa | NAARPQCPVG | LsTLAFPSpa |
| Dm Pellino | 13 | LCGATLLWRs | AeGLqHsPTk | hdLEkLidaI | NAgRPQCPVG | LNTLviPrkv |
| Ci Pellino | 14 | LCGATLLWRs | sshercmPTp | lHideLihkl | NlgRPQCPVG | LtTLAFPrrs |
| Ce Pellino | 15 | LCGATiLWRT | AdGLersPkm | reLEmaldrl | sAgRPQCPVn | LNTLviPkkr |
| consensus |  | LCGATLLWRT | A-GL-HTPT- | KHLEALRQEI | NAARPQCPVG | LNTLAFPS-- |

|  |  | 351 | | | | 400 |
|---|---|---|---|---|---|---|
| Hs Pellino-1 | 4 | R.KDVVDEKQ | PWVYLNCGHV | HGYHNWGnkE | ERdgkdRECP | MCRSVGP.YV |
| Mm Pellino-1 | 2 | R.KDVVDEKQ | PWVYLNCGHV | HGYHNWGnkE | ERdgkdRECP | MCRSVGP.YV |
| Hs Pellino-2 | 8 | R.KeVVeEKQ | PWaYLsCGHV | HGYHNWGhRs | dteAnERECP | MCRtVGP.YV |
| Mm Pellino-2 | 6 | R.KeVVeEKQ | PWaYLsCGHV | HGYHsWGhRs | daeAnERECP | MCRtVGP.YV |
| Hs Pellino-3 | 12 | RgrtapDkqQ | PWVYvrCGHV | HGYHgWGcRr | ERGpqERECP | lCRlVGP.YV |
| Dm Pellino | 13 | nigDqVn..Q | PyVYLNCGHV | gGhHdWGqdE | ntGA..RrCP | MClelGP.vV |
| Ci Pellino | 14 | katket.EKQ | PWVYLqCGHV | HGrieWGyqg | E...eERiCP | lCRSVGk.YV |
| Ce Pellino | 15 | ngrq.inrrQ | PyVYLqCGHV | qGrHeWGvqE | nsGqrsgkCP | iClveseriV |
| consensus |  | R-KDVVDEKQ | PWVYLNCGHV | HGYHNWG-RE | ERGA-ERECP | MCRSVCP-YV |

|  |  | 401 | | | | 450 |
|---|---|---|---|---|---|---|
| Hs Pellino-1 | 4 | PLWLGCEAGF | YVDAGPPTHA | FsPCGHVCSE | KTtaYWSQIP | LPHGTHtFHA |
| Mm Pellino-1 | 2 | PLWLGCEAGF | YVDAGPPTHA | FsPCGHVCSE | KTtaYWSQIP | LPHGTHtFHA |
| Hs Pellino-2 | 8 | PLWLGCEAGF | YVDAGPPTHA | FtPCGHVCSE | KsAKYWSQIP | LPHGTHAFHA |
| Mm Pellino-2 | 6 | PLWLGCEAGF | YVDAGPPTHA | FtPCGHVCSE | KsAKYWSQIP | LPHGTHAFHA |
| Hs Pellino-3 | 12 | PLWLGqEAGl | clDpGPPsHA | FaPCGHVCSE | KTArYWaQtP | LPHGTHAFHA |
| Dm Pellino | 13 | tLcmGlEpaF | YVDvGaPTyA | FnPCGHmatE | KTvKYWanve | iPHGThgFqA |
| Ci Pellino | 14 | PLWvGgEpaF | YVDiGPPsyc | FvPCGHVCSq | KTAiYWSQta | LPHGTqAysA |
| Ce Pellino | 15 | qLsmGmEpsF | hlDsGvldHt | FnPCGHmaSk | qTvlYWSrIP | LPqGTcrydp |
| consensus |  | PLWLGCEAGF | YVDAGPPTHA | F-PCGHVCSE | KTAKYWSQIP | LPHGTHAFHA |

|  |  | 451 | | 486 | | |
|---|---|---|---|---|---|---|
| Hs Pellino-1 | 4 | ACPFCAhQLA | GEQGYIrLIF | QGPLD*~~~~ | ~~~~~~ | |
| Mm Pellino-1 | 2 | ACPFCAhQLA | GEQGYIrLIF | QGPLD*~~~~ | ~~~~~~ | |
| Hs Pellino-2 | 8 | ACPFCATQLv | GEQncIkLIF | QGPiD*~~~~ | ~~~~~~ | |
| Mm Pellino-2 | 6 | ACPFCATQLv | GEQncIkLIF | QGPvD*~~~~ | ~~~~~~ | |
| Hs Pellino-3 | 12 | ACPFCgawLt | GEhGcvrLIF | QGPLD*~~~~ | ~~~~~~ | |
| Dm Pellino | 13 | vCPFCATpLd | GatGYIkLIF | QdnLD~~~~~ | ~~~~~~ | |
| Ci Pellino | 14 | ACPFCATpLe | GdlGYkkLIF | QqPLD~~~~~ | ~~~~~~ | |
| Ce Pellino | 15 | vCPFCyqlLA | tErpfvrLIF | Qdncfdddti | rfsnea | |
| consensus |  | ACPFCATQLA | GEQGYI-LIF | QGPLD----- | ------ | |

The human Pellino-1, -2, and -3 coding sequences were compared with publicly available preliminary human genomic DNA sequences, and the following chromosome 2, 14, and 11 contigs were identified as containing human Pellino-1, -2, and -3 coding sequences, respectively: AC013466.3 (Pellino-1), AL138995.4 and AL355073.4 (Pellino-2), and AC027270.3 (Pellino-3). The approximate positions of the exons containing Pellino-1, -2, and -3 coding sequences in the above contigs are shown in the table below, along with their locations relative to SEQ ID NOs 3, 7, and 11; note that the 5' and 3' untranslated regions may extend further along the contig sequence beyond those portions that correspond to SEQ ID NOs 3, 7, and 11, as indicated by the parentheses around the contig endpoints in the table. Note also that the positions of exon boundaries are very highly conserved within the human Pellino-1, -2, and -3 coding sequences, with the differences in exon size primarily occurring in Exon 1, with Pellino-2 having two additional codons in Exon 1 relative to Pellino-1, and Pellino-3 having 27 additional codons in Exon 1 relative to Pellino-1. Due to the preliminary sequence and assembly of the contig sequence, the exons within the contig are not always in the right order or orientation with respect to each other, and may contain sequence variations due to inaccurate sequence data or allelic polymorphism. For example, the genomic contig AC013466.3 has two copies of the Pellino-1 Exon 2 sequence present in opposite orientations with respect to each other, as indicated in the table below.

| Position of Pellino-1 exons in AC013466.3 | Position in SEQ ID NO: 3 |
|---|---|

-continued

| | | |
|---|---|---|
| Exon 1 | (32275)–32205 | 1–71 |
| Exon 2 | 28794–28666; 74461–74589 | 72–201 |
| Exon 3 | 78789–78890 | 202–303 |
| Exon 4 | 82682–82879 | 304–501 |
| Exon 5 | 82979–83167 | 502–690 |
| Exon 6 | 84024–(84590) | 691–1257 |

| | Position of Pellino-2 exons in AL138995.4 | Position in SEQ ID NO: 7 |
|---|---|---|
| Exon 1 | (81889)–81965 | 1–77 |
| Exon 2 | 141562–141691 | 78–207 |

| | Position of Pellino-2 exons in AL355073.4 | Position in SEQ ID NO: 7 |
|---|---|---|
| Exon 3 | 81379–81480 | 208–309 |
| Exon 4 | 90140–90337 | 310–507 |
| Exon 5 | 91971–92159 | 508–696 |
| Exon 6 | 98303–(98869) | 697–1263 |

| | Position of Pellino-3 exons in AC027270.3 | Position in SEQ ID NO: 11 |
|---|---|---|
| Exon 1 | (16496)–16646 | 1–152 |
| Exon 2 | 19608–19737 | 153–282 |
| Exon 3 | 75962–76063 | 283–384 |
| Exon 4 | 76834–77027 | 385–579 |
| Exon 5 | 77329–77521 | 580–772 |
| Exon 6 | 79193–(79754) | 773–1338 |

The genomic sequences comprising human Pellino-1 exons map to the 2p13.3 region of human chromosome 2. Human Pellino nucleic acids such as SEQ ID NO:3 and fragments thereof are useful for the cytological identification of this chromosomal region, and for the genomic mapping of human genetic disorders such as the following disorders that have been mapped to this region: Preeclampsia/Eclampsia gene 1, Alstrom Syndrome, Parkinson Disease gene 3, Orofacial Cleft gene 2, and Welander Distal Myopathy. The genomic sequences comprising human Pellino-2 exons map to the 14q24.3 region of human chromosome 14. Human Pellino nucleic acids such as SEQ ID NO:7 and fragments thereof are useful for the cytological identification of this chromosomal region, and for the genomic mapping of human genetic disorders such as the following disorders that have been mapped to this region: Achromatopsia gene 1, Hereditary Benign Chorea, Multinodular Goiter, Myopathy (Distal), Tyrosinemia Type 1B, and Alzheimer's Disease gene 3. The genomic sequences comprising human Pellino-3 exons map to a region of human chromosome 11 between 11p11.1 and 11q13, and are believed to map most closely to the 11q12.1 region. Human Pellino nucleic acids such as SEQ ID NO:3 and fragments thereof are useful for the cytological identification of this chromosomal region, and for the genomic mapping of human genetic disorders such as the following disorders that have been mapped to this region: Osteoporosis-Pseudoglioma Syndrome and Spinocerebellar Ataxia gene 5. Given a recent report (Schmitt-John et al., 2000, "Mouse Homologue of the *Drosophila* pellino Gene, Pli1 on Chr 11 is Affected in the Wobbler Mutant", Abstract B12 posted at imgs.org/abstracts/2000abstracts/toc_b.html) suggests that murine Pellino-1 may be the protein affected in the Wobbler mutant, which exhibits degeneration of spinal motoneurons, it is intriguing that all three of the human Pellino genes map near human genetic loci involving neuromuscular defects: Welander Distal Myopathy; Myopathy (Distal); and Spinocerebellar Ataxia gene 5 (which involves failure of muscular coordination and/or irregularity of muscular action), suggesting that these human genetic defects may involve defects in human Pellino.polypeptide activity.

EXAMPLE 2

Reporter Gene Assays of Pellino Polypeptide Activity

The murine Pellino-1 coding sequence DNA was fused, in frame at the 3' end, to DNA encoding the FLAG epitope, followed by an in-frame stop codon. This construct was cloned into the mammalian expression vector pDC304 (identical to pDC302, described in U.S. Pat. No. 5,599,905, issued Feb. 4, 1997, except that the early splice region, consisting of splice donor and acceptor sites of the SV40 viral element, has been removed); and transfected into an IL-1-responsive line of COS-7 cells by the DEAE-dextran method.

In order to assay the effect of the Pellino-1-FLAG polypeptide and other forms of Pellino polypeptides on reporter gene activity, a method essentially as described in Born et al., 1998, *J. Biol. Cheni.* 273: 29445–29450 (which is incorporated by reference herein) can be used. As one example of this method, Cos7 cells were transiently transfected by the DEAE-dextran method as described (Cosman et al., 1984, *Nature* 312: 768–771, which is incorporated by reference herein), using 150 ng of the Pellino polypeptide expression construct and 700 ng of the reporter plasmid per 45,000 cells. Two days post-transfection, cells were stimulated with 10 ng/ml IL-1 or 40 ng/ml IL-18 (PeproTech, Inc.) for 4 hours. Cells were lysed and luciferase activity assessed using Reporter Lysis Buffer and Luciferase Assay Reagent (Promega Corp.). IL-8 promoter-reporter and NFkB-dependent reporter constructs may be used as reporter plasmids. Alternatively, the effect of Pellino polypeptide expression may be assayed in COS-1 cells. In an alternative preferred method, COS7 cells were grown in 12-well dishes as described above. The cells were transiently transfected with Pellino test plasmid, 50 ng of reporter plasmid DNA, and empty vector, as required, to a total of 1 micrograms of total DNA per well. After 24 hours, stimulating agents were added in a small amount (less than 0.5% final volume) of medium or dimethyl sulfoxide, and the cells were re-incubated for 5 hours. Cells were lysed in luciferase Reporter Lysis Buffer (Promega, Madison Wis., 0.25 ml per well) and luciferase activity was measured in a EG & G/Berthold luminometer after addition of Luciferase Assay Reagent (Promega) according to the supplier's instructions. All results were normalized to total protein content of the lysates as measured using the micro-BCA assay (Pierce, Rockford, Ill).

In a preliminary experiment, expression of murine Pellino-1-FLAG in this manner was found to partially inhibit IL-1-induced NFkB-dependent reporter gene activity. This inhibitory effect of Pellino-1-FLAG may have been due to over-expression of the Pellino polypeptide, as transfecting COS cells with high concentrations of a Pellino-1- or Pellino-2-expressing construct has been demonstrated to have an inhibitory effect on NFkB-dependent reporter gene activity, possibly through the formation of homodimers or higher multimers of Pellino polypeptides that could have inhibitory effects in contrast to stimulatory effects of moderate concentrations of Pellino polypeptide monomers. Other possibilities for the inhibitory effect of a preparation of Pellino-1-FLAG on NFkB-dependent reporter gene activity are the presence of mutated forms of the polypeptide as described below, or the relative presence or absence of a yet-to-be-characterized factor in a particular cell line.

However, in later experiments with a murine Pellino-1-FLAG construct that was confirmed to comprise a wild-type Pellino-1 amino acid sequence, the wild-type Pellino-1-FLAG polypeptide had a stimulatory effect on IL-1-induced NF-kB-dependent reporter gene activity (see Table 2, below); wild-type Pellino-1-FLAG also moderately augmented Jun N-terminal kinase, p38 kinase, and ERK signaling mediated by IL-1. When expressed in COS-1 cells, wild-type Pellino-1 polypeptide stimulates IL-8 promoter-reporter gene activity and NF-kB-dependent reporter activity in both the presence and absence of treatment with TNF-alpha, as compared to a vector-only control. In similar experiments, transfection of COS cells with moderate amounts of construct expressing wild-type Pellino-2 polypeptide also stimulates NF-kB-dependent reporter gene activity.

To define regions of Pellino that determine its response to pro-inflammatory mediators, a number of mutant Pellino expression vectors were constructed. The apparent Mr of FLAG-Pellino-1 on SDS-PAGE gels is close to the value of 47,224 daltons calculated from the primary sequence, indicating a lack of extensive post-translational modification. It is therefore possible to predict the approximate point in the primary sequence of Pellino-1 where cleavage should occur in order to generate a 30-kDa N-terminal product. The closest residue to this theoretical point is Phe-158; cleavage of the peptide bond preceding this residue would result in a polypeptide with a mass of 30,044 daltons. This region of Pellino-1 polypeptide was therefore chosen for mutation, since it might be expected that some of the resulting mutants would be resistant to cleavage, or otherwise altered in their response to pro-inflammatory stimuli. Cleavage of Pellino is sensitive to a chymotrypsin inhibitor, TPCK, and chymotrypsin has a requirement for a large, aromatic residue on one side of its cleavage site. Reasoning that the Pellino-cleaving enzyme might share the same specificity determinants, we chose to mutate four of the aromatic amino acids that are invariably found in this region in the mammalian Pellino polypeptides. The two internal deletion mutants were chosen to flank the predicted cleavage site, and also to include highly conserved residues. In addition, a series of truncation mutants, deleting residues from both amino- and carboxyl-termini, and mutants lacking conserved cysteine residues in the RING-finger-like domain, were constructed as follows. To make a series of N-terminal deletions, short sense-strand oligonucleotide primers were synthesized in which a sequence containing a KpnI restriction site and a methionine codon was fused to murine Pellino-1 sequences beginning with the codons for Gly-51, Phe-100, Asp-181, and Val-231. These were used with an antisense FLAG-BglII-adapted primer to amplify PCR fragments from murine Pellino-1-FLAG template DNA. These fragments were re-cloned into pDC304 vector to generate, respectively, the constructs encoding the dN50-FLAG, dN99-FLAG, dN180-FLAG, and dN230-FLAG mutants. A similar strategy was used to construct a series of mutants progressively truncated at the C-terminus; antisense oligonucleotides terminating with the codons for Thr-150, Thr-250, and Glu-350 were synthesized in tandem with a sequence containing a stop codon and a BglII restriction site. These primers were used to generate PCR fragments which were subsequently cloned into pDC304 and referred to as encoding the 1–150, 1–250, and 1–350 mutants, respectively. The constructs encoding the single amino-acid substitutions F137L-FLAG, Y154A-FLAG, F158A-FLAG, and F165L-FLAG were constructed using the QuickChange site-directed mutagenesis kit (Stratagene, LaJolla, Calif.). To construct the internal deletion mutants, dl33–156-FLAG and dl55–158-FLAG, we made, in each case, a pair of PCR fragments containing a restriction site introduced to flank the sequence to be deleted. Following restriction digestion and purification of the PCR fragment pairs, they were three-way ligated into pDC304 vector. A mutant was also constructed in which four RING-finger-like domain amino acids from Cys-333 through Cys-336 were replaced by the two-amino-acid sequence Gly-Ser; this mutant is referred to as C333-C336GS-FLAG.

In contrast to the effect of wild-type Pellino-1, mutant forms of Pellino-1 polypeptides with amino acids 133–156 or amino acids 155–158 of SEQ ID NO:2 deleted, or with 50 or 99 amino acids of the N-terminal region of the polypeptide deleted, or with substitutions in the RING-finger-like domain that remove cysteine residues, inhibited IL-8 promoter-reporter gene activity in both the presence and absence of treatment with TNF-alpha, and the mutant form of Pellino-1 with amino acids 155–158 deleted inhibited NF-kB-dependent reporter activity in both the presence and absence of treatment with PMA, as compared to a vector-only control. Stimulation of the activity of these reporter genes is consistent with a stimulatory effect on a pro-inflammatory regulatory cascade, while inhibition of the activity of these reporter genes is consistent with an inhibitory effect on a pro-inflammatory regulatory cascade. A summary of the effects of wild-type and mutant forms of murine Pellino-1 on NF-kB-dependent reporter gene activity is summarized in Table 2; all amino acid positions are in reference to the amino acid sequence of SEQ ID NO:2. The "Soluble or Insoluble" and "Cleaved?" results are described in Examples 3 and 4 below.

It can be seen from the Table below that deleting some of the N-terminal region of the Pellino-1 polypeptide (i.e. deleting the N-terminal 50 or 99 amino acids) generates mutants having inhibitory activity on MAP kinase-activated signaling pathways (as demonstrated for example by inhibition of NF-kB-dependent transcription), but deleting more substantial portions (i.e. the N-terminal 180 or 230 amino acids) abolishes the ability of Pellino-1 to stimulate or to inhibit reporter gene activity. Therefore, it should be possible to make additional N-terminal deletion mutants of Pellino polypeptides having inhibitory activity on NF-kB-dependent transcription, for example, a mutant in which N-terminal amino acids corresponding to the 105, 110, 115, 120, 125, 130, 135, 140, 145, 150, 155, 160, 165, 170, or 175 N-terminal amino acids of SEQ ID NO:2 are deleted, but which still retains inhibitory activity. Alternatively, other residues within the N-terminal amino acids of Pellino polypeptides corresponding to the 180 N-terminal amino acids of SEQ ID NO:2 may be deleted in order to generate mutant forms of Pellino polypeptides having inhibitory activity on NF-kB-dependent transcription. Similarly, mutants in which deletions (of one to 50 amino acids and more preferably one to 30 amino acids) are made within the central conserved domain and the RING-finger-like domain may also exhibit inhibitory activity on NF-kB-dependent transcription. All such mutants can be readily tested for activity using the reporter gene assays described herein.

TABLE 2

| Form of Pellino-1 | Description | Soluble or Insoluble | Cleaved? | Effect on Reporter Gene |
|---|---|---|---|---|
| wild-type-FLAG | unaltered Pellino-1 | Soluble | + | Stimulatory |
| d133-156-FLAG | amino acids 133–156 deleted | Insoluble | + | Inhibitory |
| d155-158-FLAG | amino acids 155–158 deleted | Insoluble | + | Inhibitory |
| dN50-FLAG | N-terminal 50 amino acids deleted | Insoluble | + | Inhibitory |
| dN99-FLAG | N-terminal 99 amino acids deleted | Insoluble | + | Inhibitory |
| dN180-FLAG | N-terminal 180 amino acids deleted | Insoluble | n/a | inactive |
| dN230-FLAG | N-terminal 230 amino acids deleted | Insoluble | n/a | inactive |
| 1–250 | only amino acids 1–250 present | Insoluble | + | inactive |
| 1–350 | only amino acids 1–350 present | Soluble | + | inactive |
| F137L-FLAG | Phe to Leu substitution at residue 137 | Soluble | + | not tested |
| Y154A-FLAG | Tyr to Ala substitution at residue 154 | Soluble | +/− | Stimulatory |
| F158A-FLAG | Phe to Ala substitution at residue 158 | Soluble | + | Slightly Stimulatory |
| F165L-FLAG | Phe to Leu substitution at residue 165 | Soluble | − | Stimulatory |
| C333-C336GS-FLAG | replacement of Cys-333 through Cys-336 with Gly-Ser | not tested | not tested | Inhibitory |

In similar experiments using COS cells transfected with a reporter construct including CHOP, a p38-dependent promoter, the d155-158-FLAG mutant form of Pellino-1 inhibited TNF-alpha stimulation of the CHOP reporter gene activity. This result is significant because it demonstrates that mutant forms of Pellino polypeptides are able to inhibit multiple MAP kinase-activated pro-inflammatory signaling pathways, as indicated by their inhibition of both NF-kB-dependent transcription and p38-dependent transcription. Because wild-type forms of Pellino polypeptides have stimulatory effects on key components of the four major MAP kinase-activated signaling pathways—stimulation of Jun N-terminal kinase, p38 kinase, and ERK signaling, and stimulation of NF-kB-dependent transcription—the "dominant-negative" mutant forms of Pellino polypeptides are expected to inhibit the Jun kinase and ERK MAP kinase-activated signaling pathways in a similar fashion to the inhibition of the p38 and NF-kB MAP kinase-activated signaling pathways.

EXAMPLE 3

Intracellular Localization of Pellino Polypeptides

This example describes a method for monitoring the regulation by IL-1 (or other cytokine or molecule) of the intracellular localization of Pellino-1 in cells. COS-7 cells (which express an endogenous IL-1 receptor) are transfected with an expression vector comprising FLAG-Pellino-1 as described in Example 2. Cells may also be transfected at the same time with other cDNAs encoding proteins which mediate inflamnatory signaling, such as IL-1 Receptor-associated kinase (IRAK; GenBank NP001560). Transfected cells are cultured for about 48 hours. IL-1 (20 ng/ml), or another cytokine or molecule at an appropriate concentration, is added to the culture medium for the last 15 minutes (short-term stimulation) or 24 hours (prolonged stimulation) of this culture period.

The cell cultures are washed with ice-cold phosphate-buffered saline (PBS), and cell lysates are prepared by scraping the cells into lysis buffer (a buffer containing 50 mM Tris-chloride pH 8.0 supplemented with 1% nonidet (NP-40), 0.5% sodium deoxycholate, 0.1 mM sodium orthovanadate, 30 mM para-nitrophenol phosphate, 30 mM beta-glycerophosphate, 140 mM NaCl, 5 mM dithiothreitol, 2 mM EDTA, 10 mM leupeptin, 10 mM pepstatin A and l mM phenymethylsulfonyl fluoride; chemicals purchased from Sigma, St. Louis, Mo.). Solubilization of the cellular proteins can be facilitated by passage of the lysates several times through 25-gauge hypodermic needles. The lysate is centrifuged at 13,000×G at 4° C. The supernatant at this stage is referred to as the "soluble fraction." The remaining pellet is solubilized in 1× SDS-PAGE sample buffer (Laemmli et al., Nature 227:680;1970); this material is referred to as the "insoluble fraction."

In an alternate, preferred, procedure for obtaining soluble and insoluble fractions comprising Pellino polypeptides, COS7 (monkey kidney) cells were maintained in Dulbecco's modified Eagles medium containing 5% fetal bovine serum and supplemented with 100 units/ml penicillin and 100 micrograms/ml streptomycin at 35° C. in 5% $CO_2$. Plasmids encoding Pellino-FLAG, or other expression plasmids, were transiently transfected into confluent COS7 cells in 6-well tissue culture dishes (Costar) using DEAE-dextran. At various times after transfection, cells were scraped into 0.4 ml of an lysis/extraction buffer consisting of 50 mM Tris-HCl pH 7.8, 1% NP-40, 0.15M NaCl, 2 mM EGTA, 5 microM NaF, 30 mM, β-glycerophosphate, 1 mM sodium orthovanadate, 1 mM dithiothreitol, 0.5 mM phenylmethylsulfonyl fluoride, 10 micrograms/ml leupeptin, and 10 micrograms/ml pepstatin A. The cell suspensions were allowed to lyse on ice for 15 minutes and were centrifuged (13000 rpm for 10 minutes at 4 degrees C) in a microcentrifuge. The supernatants were carefully removed to fresh tubes and diluted with one-third volume of 4×-concentrated SDS-PAGE sample buffer containing 2-mercaptoethanol. The supernatant samples ('detergent-soluble' fraction) were boiled for 5 minutes. The pellets were re-extracted by resuspending them in one half the original volume of 1×-concentrated SDS-PAGE sample buffer, vortexing, and then boiling them.

Matched aliquots of soluble fraction and insoluble fraction may then be analyzed by gel electrophoresis on 4–20% gradient SDS-polyacrylamide gels (Novex, Invitrogen Corp., Carlsbad Calif.), and transferred to nitrocellulose membranes, and assayed by western immunoblotting using anti-FLAG antibodies (i.e., FLAG M2) to bind to the protein products of the transfected cDNAs. Proteins are visualized by incubation of western blots with horseradish-peroxidase-conjugated anti-mouse IgG (BioRad, San Diego, Calif.) followed by detection using the ECL system (Amersham; Arlington Heights, Ill.).

EXAMPLE 4

Effect of Cell Stimulation on Pellino Polypeptide Localization and Cleavage

This example describes the effect of stimulation of COS-7 cells transfected with an expression vector encoding FLAG-Pellino-1 with IL-1 or other molecules. Transfected cells are prepared substantially as described above. In some instances, the cells are co-transfected with a pDC304 vector containing a cDNA insert coding for human IRAK with a tandem 3' FLAG and poly-His 'tail.' In further instances, the cells are co-transfected with a catalytically inactive human FLAG-polyHis-IRAK expression vector in which lysine residue 293 in the ATP-binding pocket of IRAK is replaced with an alanine. As Drosophila Pellino was identified by its ability to associate with Pelle, experiments in which Pellino is coexpressed with IRAK have been performed to determine if mammalian Pellino interacted with IRAK, the presumptive mammalian counterpart of Pelle.

Analysis indicated that in the absence of over-expressed, active IRAK, FLAG-Pellino-1 is largely present in the soluble fraction as a polypeptide close to the predicted size of 46 kDa. When IRAK is over expressed, FLAG-Pellino-1 is largely found in the insoluble fraction, and a significant portion of the Pellino in the insoluble fraction appeared on Western blots as a 30-kDa species. Since it was reactive with anti-Flag antibody, the 30-kDa species presumably consists of an amino-terminal fragment. In some experiments, in which larger amounts of expression plasmid cDNA were used, an additional Pellino N-terminal cleavage product of 17 kDa was detected. The 30-kDa insoluble form of Pellino-1 present in cells transfected with wild-type IRAK migrated slightly slower than that from cells co-transfected with kinase-inactive IRAK, which might indicate that the 30-kDa Pellino-1 fragment was differently phosphorylated, or perhaps modified in some other way. Similarly, there was an overall shift in the mobility of wild-type IRAK evident in cells which were co-transfected with Pellino-1, consistent with a model in which both kinase-active IRAK and Pellino are involved in the regulation of the state of the other's post-translational modifications (modifications such as phosphorylation, ubiquitinylation, myristoylation, farnesylation, and geranylgeranylation), but kinase-inactive IRAK can neither affect modifications to Pellino-1 nor be affected in this way by Pellino-1. In contrast, the cleavage of Pellino-1 and relocation to the insoluble fraction do not require the kinase activity of IRAK.

To determine if the observed redistribution and proteolytic processing of Pellino-1 specifically required IRAK, Pellino-1-transfected cells were stimulated with agents that activate NF-kB by IRAK-independent pathways such as phorbol myristate acetate (PMA, 100 ng/ml), which is known to promote many of the same intracellular signals as IL-1, and TNF-alpha (20 ng/ml). TNF-alpha activates NF-kB through a mechanism involving the adaptor protein TRADD, the kinase RIP, and TRAF2, while PMA stimulates the activity of protein kinase C which is known to cross-talk with the NF-kB pathway. Both agents caused a time-dependent increase in the redistribution of Pellino-1 into the insoluble fraction, where it was mostly present as the 30-kDa cleavage product. In both cases, 2 to 3 hours of exposure to the stimulus was required before significant Pellino cleavage was seen. The total amount of detectable Pellino-1 polypeptide (the sum of soluble and insoluble fractions) was increased in the presence of PMA or TNF-alpha, which presumably reflects a change in the net rates of Pellino-1 synthesis and/or degradation. However, incubation with various growth factors (epidermal growth factor (EGF), basic fibroblast growth factor, transforming growth factor-beta, or platelet-derived growth factor) had little or no effect on Pellino-1; only epidermal growth factor was very weakly active. EGF has been reported in some cells to activate NF-kB through the induction of IkB-alpha degradation. These results are consistent with Pellino-1 cleavage and redistribution occurring specifically in response to stimuli which activate NF-kB, including those with signaling mechanisms not involving IRAK. . Time-course experiments demonstrated that the cleavage and relocation of Pellino-1 began at about two hours after induction with PMA, and at about three hours after induction with TNF-alpha, whereas TNF-alpha-mediated NF-kB activation is maximal in COS7 cells after 15 minutes, suggesting that cleavage and changes in the solubility of Pellino-1 are more likely to be part of the cellular effects of NF-kB activation than to be causally involved in the activation process, and indicating that Pellino-1 cleavage and relocation might depend upon de novo protein synthesis. This observation was supported by experiments in which pretreatment of FLAG-Pellino-1-transfected cells with the protein synthesis inhibitor cycloheximide largely prevented the ability of PMA to subsequently induce Pellino-1 cleavage and relocation.

In an effort to determine which protease might be involved in the regulation of Pellino-1 cleavage, COS7 cells transfected with a Pellino-1-expressing construct were treated with PMA together with inhibitors of different classes of proteinases as shown in Table 3 below.

TABLE 3

Effects of Various Protease Inhibitors on Pellino-1 Cleavage and Relocation

| Inhibitor | Enzyme Inhibited | Effect |
| --- | --- | --- |
| Lactacystin (20 microM) | 20S proteasome | none |
| MG132 (10 microM) | 26S proteasome | none |
| Z-VAD-FMK (20 microM) | Caspases 1, 3, 4, 7 | none |
| Z-DEVD-FMK (20 microM) | Caspases 3, 6, 7, 8, 10 | none |
| ALLN (20 microM) | Calpains 1 & 2, Cathepsins B & L, Neutral cysteine proteases | none |
| Cycloheximide (40 microM) | Protein synthesis | inhibition |
| TPCK (20 microM) | Serine proteases (Chymotrypsins) | inhibition |

These results indicated that a member of the chymotrypsin-like serine protease family was involved in the cleavage and relocation of Pellino-1. This is in contrast to other, known pathways of IL-1 and/or TNF-alpha signaling, which were shown to involve caspase activation (for example, TNF-induced apoptosis; Rath et al., *J. Clin. Immunol.* 19:350, 1990), or the proteasome (for example, IL-1-induced degradation of IkB; Karin et al., *Semin. Immunol.* 2000. 12:85, 2000). The slow kinetics of Pellino-1 processing would be consistent with a requirement for de novo protein synthesis, consistent with this, treatment of COS7 cells with the protein synthesis inhibitor cycloheximide completely prevented its PMA-induced cleavage. It is therefore possible that PMA induces the synthesis of a proteinase which cleaves Pellino, or the synthesis of some accessory factor for a constitutively-expressed proteinase. These results have additional important implications for the mechanism involved in Pellino polypeptide processing. MG-132 (26) and ALLN (27, 28), through their ability to prevent the proteasome-mediated degradation of IkB, are both potent inhibitors of NF-kB activation. It follows that Pellino processing, which is insensitive to MG132 and ALLN, cannot be dependent upon cellular events downstream of IkB degradation. Although TPCK is also well-established as an inhibitor of IkB degradation, the fact that the other proteasome inhibitors do not block Pellino-1 cleavage, as discussed above, excludes this as the underlying mechanism for TPCK's effectiveness.

For a 30 kDa Pellino-1 fragment to be generated, proteolytic cleavage would be predicted to occur within the region of amino acids 132 to 189 of SEQ ID NO:2. Examination of the amino acid sequence of Pellino-1 shows it has been extremely well conserved in those species for which EST sequence data is available (murine and human Pellino-1 and Pellino-2, disclosed herein; *Drosophila* pellino, GenBank accession number AF091624; and the F25B4.2 gene product of *Caenorhabditis elegans*, GenBank accession number U64842). A number of conserved phenylalanine and tyrosine residues are present in this region, any of which might serve as the recognition site for a chymotrypsin-like serine protease.

EXAMPLE 5

GST-Pellino Fusion Polypeptides

This example describes the construction and expression of a recombinant Glutathione S-transferase (GST)-Pellino-1 fusion protein. PCR primers were synthesized having the sequences ATATTCACTGAATTCTGATGTTTTCTC-CTGATCAA (Primer 1; SEQ ID NO:9) and AGTGAATAT-GAATTCCTACTTATCATCGTCATCTTTG (Primer 2; SEQ ID NO:10), for the sense and antisense primers, respectively. These were designed for use with a Pellino-1-FLAG template, and add a EcoR1 site to each end of the amplified product. This PCR product was ligated into the unique EcoR1 cloning site of the vector pGEX2T (described in EP 0293249-A) such that the coding sequences of the glutathione S-transferase gene and FLAG-Pellino-1 were in the same frame. *E coli* strain DH10B were transformed with the resultant vector and a one-liter culture was grown. Transcription of the GST-Pellino-1-FLAG gene was induced by addition of IPTG (0.1 mM) to the bacterial culture for three hours. Bacterial cells were harvested and lysed according to methods well known in the art (see, for example, Smith D. B., Johnson K. S.; *Gene* 67:31–40(1988)). The lysate containing solubilized GST-Pellino-1-FLAG was purified on 1 ml of Glutathione-Agarose beads (Pharmacia), according to the directions supplied by the manufacturer.

EXAMPLE 6

Anti-Pellino Monoclonal Antibodies

This example illustrates the preparation of monoclonal antibodies against Pellino polypeptides. Preparations of purified recombinant Pellino polypeptides, for example, or transfected cells expressing high levels of Pellino polypeptides, are employed to generate monoclonal antibodies against Pellino polypeptides using conventional techniques, such as those disclosed in U.S. Pat. No. 4,411,993. DNA encoding Pellino polypeptides can also be used as an immunogen, for example, as reviewed by Pardoll and Beckerleg in *Immunity* 3:165, 1995. Such antibodies are likely to be useful as components of diagnostic or research assays for Pellino or Pellino activity, or in affinity purification of Pellino polypeptides.

To immunize rodents, Pellino immunogen (for example, a Pellino-1 peptide comprising amino acids 2 through 20, amino acids 118 through 131, or amino acids 318 through 340 of SEQ ID NOs 2 and 4) preferably coupled to an immunogenic molecule such as keyhole limpet hemocyanin, is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 micrograms subcutaneously into a selected rodent, for example, BALB/c mice or Lewis rats. DNA may be given intradermally (Raz et al., *Proc. NatL Acad. Sci. USA* 91:9519, 1994) or intramuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with Pellino polypeptides, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144: 4212 (1990). Positive clones are then injected into the peritoneal cavities of syngeneic rodents to produce ascites containing high concentrations (<1 mg/ml) of anti-Pellino monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to Pellino polypeptide.

EXAMPLE 7

Northern Blot Analysis of Pellino-1 Expression

A 234-bp PCR fragment corresponding to the predicted 3' end of the human Pellino-1 mRNA was generated by standard amplification methods. The PCR fragment was purified (Qiagen PCR purification kit) and labeled by the Gibco Random Prime Oligonucleotide DNA Labeling kit. The cDNA riboprobe was denatured at 100 degrees C. for 5 minutes and placed on ice. The cDNA probe was denatured at 100 degrees C. for 5 minutes before being added to the hybridization solution. A multi-tissue northern blot containing RNA from human tissues—brain, heart, skeletal muscle, colon (no mucosa), thymus, spleen, kidney, liver, small intestine, placenta, lung, and peripheral blood leukocytes—was purchased from Clonetech (Palo Alto, Calif.). The blot was blocked in 5 mL ExpressHyb Solution for 30 minutes at 68 degrees C. Fresh ExpressHyb solution containing the denatured radiolabeled cDNA probe was added to the membrane and incubated at 68 degrees C. for 1 hour with continuous shaking. The blot was rinsed in 2× SSC, 0.05% SDS with four changes at room temperature for 40 minutes, followed by a wash in 0.1× SSC, 0.1% SDS with two changes for 40 minutes at 50 degrees C. The riboprobe for Pellino-1 hybridized to the Northern blot with a major band at 4.4 kilobases in all tissues represented, with an increased level of expression evident in peripheral blood leukocytes, lung, placenta, liver, kidney, skeletal muscle, and brain. The message appears to be more highly expressed in peripheral blood leukocytes, and in this tissue there seems to be two additional bands at 7.5 and 9.5 kb which do not appear in the lanes for the other tissues. The cDNA for human Pellino-1 is predicted to include 1251 base pairs in the coding region and 1931 base pairs in the 3' untranslated region, and no evidence for alternative splicing has yet been identified.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention. The relevant disclosures of references cited herein are specifically incorporated by reference.

| SEQ ID NO | Sequence Type | Description |
| --- | --- | --- |
| SEQ ID NO: 1 | Nucleotide | Murine (*Mus musculus*) Pellino-1 coding sequence |
| SEQ ID NO: 2 | Amino acid | Murine (*Mus musculus*) Pellino-1 amino acid sequence |
| SEQ ID NO: 3 | Nucleotide | Human (*Homo sapiens*) Pellino-1 coding sequence |
| SEQ ID NO: 4 | Amino acid | Human (*Homo sapiens*) Pellino-1 amino acid sequence |
| SEQ ID NO: 5 | Nucleotide | Murine (*Mus musculus*) Pellino-2 coding sequence |
| SEQ ID NO: 6 | Amino acid | Murine (*Mus musculus*) Pellino-2 amino acid sequence |
| SEQ ID NO: 7 | Nucleotide | Human (*Homo sapiens*) Pellino-2 coding sequence |
| SEQ ID NO: 8 | Amino acid | Human (*Homo sapiens*) Pellino-2 amino acid sequence |
| SEQ ID NO: 9 | Nucleotide | PCR primer |
| SEQ ID NO: 10 | Nucleotide | PCR primer |
| SEQ ID NO: 11 | Nucleotide | Human (*Homo sapiens*) Pellino-3 coding sequence |
| SEQ ID NO: 12 | Amino acid | Human (*Homo sapiens*) Pellino-3 amino acid sequence |
| SEQ ID NO: 13 | Amino acid | Fruit fly (*Drosophila melanogaster*) Pellino (GenBank AAC96298) |
| SEQ ID NO: 14 | Amino acid | Ascidian (Sea squirt, *Ciona intestinalis*) Pellino (GenBank BAB00628) |
| SEQ ID NO: 15 | Amino acid | Nematode (*Caenorhabditis elegans*) Pellino (GenBank CAB97346) |

```

We claim:

1. An isolated Pellino central domain polypeptide comprising amino acids 134 through 195 of SEQ ID NO:8.

2. An isolated nucleic acid encoding a polypeptide according to claim 1.

3. A vector comprising a nucleic acid according to claim 2.

4. A recombinant host cell comprising a vector according to claim 3.

5. A process for preparing a polypeptide comprising culturing a recombinant host according to claim 4 under conditions promoting expression of the polypeptide.

6. An isolated Pellino RING finger-like domain polypeptide comprising amino acids 335–400 of SEQ ID NO:8.

7. An isolated nucleic acid encoding a polypeptide according to claim 6.

8. A vector comprising a nucleic acid according to claim 7.

9. A recombinant host cell comprising a vector according to claim 8.

10. A process for preparing a polypeptide comprising culturing a recombinant host according to claim 9 under conditions promoting expression of the polypeptide.

11. An immunogenic polypeptide consisting of at least 16 or at least 32 contiguous amino acids of SEQ ID NO:8.

12. An isolated mutant Pellino-1 polypeptide comprising a polypeptide of SEQ ID NO:8 having a mutation selected from the group consisting of:
   (a) deletion of amino acids 133–156;
   (b) deletion of amino acids 155–158;
   (c) deletion of amino acids 1–50;
   (d) deletion of amino acids 1–99;
   (e) deletion of amino acids 1–x where x is an integer between 50 and 99;
   (f) replacement of Cys-333-Cys336 with Gly-Ser; and
   (g) combinations of two or more of the mutations of (a)–(e).

wherein the mutant Pellino polypeptide is capable of inhibiting NF-kappaB-dependent transcription.

13. An isolated nucleic acid encoding a polypeptide according to claim 12.

14. A vector comprising a nucleic acid according to claim 13.

15. A recombinant host cell comprising a vector according to claim 14.

16. A process for preparing a polypeptide comprising culturing a recombinant host according to claim 15 under conditions promoting expression of the polypeptide.

* * * * *